US010226503B2

(12) United States Patent
Ling

(10) Patent No.: US 10,226,503 B2
(45) Date of Patent: *Mar. 12, 2019

(54) PLANT EXTRACT COMPOSITION FOR REDUCING TOPICAL FAT AND PROMOTING WEIGHT LOSS AS WELL AS APPLICATIONS THEREOF

(71) Applicant: Caliway Biopharmaceuticals Co., Ltd., New Taipei (TW)

(72) Inventor: Yu-Fang Ling, Taipei (TW)

(73) Assignee: CALIWAY BIOPHARMACEUTICALS CO., LTD., New Taipei (TW)

( * ) Notice: Subject to any disclaimer, the term of this patent is extended or adjusted under 35 U.S.C. 154(b) by 118 days.

This patent is subject to a terminal disclaimer.

(21) Appl. No.: 15/440,469

(22) Filed: Feb. 23, 2017

(65) Prior Publication Data

US 2017/0157195 A1  Jun. 8, 2017

Related U.S. Application Data

(63) Continuation-in-part of application No. 14/914,971, filed as application No. PCT/CN2015/088340 on Aug. 28, 2015, now Pat. No. 9,987,325.

(60) Provisional application No. 62/299,702, filed on Feb. 25, 2016, provisional application No. 62/042,864, filed on Aug. 28, 2014.

(51) Int. Cl.
*A61K 36/00* (2006.01)
*A61K 36/9066* (2006.01)
*A61K 31/05* (2006.01)
*A61K 9/00* (2006.01)

(52) U.S. Cl.
CPC ........ *A61K 36/9066* (2013.01); *A61K 9/0014* (2013.01); *A61K 9/0019* (2013.01); *A61K 31/05* (2013.01)

(58) Field of Classification Search
CPC .................................................. A61K 36/00
See application file for complete search history.

(56) References Cited

U.S. PATENT DOCUMENTS

| 6,475,530 B1* | 11/2002 | Kuhrts ................... A61K 31/74 424/725 |
| 7,977,319 B1 | 7/2011 | Levine |
| 2004/0146539 A1* | 7/2004 | Gupta ................... A61K 8/0212 424/401 |
| 2012/0177623 A1 | 7/2012 | Naghavi et al. |
| 2013/0202572 A1 | 8/2013 | Hastings |
| 2013/0273175 A1 | 10/2013 | Finley |
| 2014/0141082 A1 | 5/2014 | Gao |

FOREIGN PATENT DOCUMENTS

| CN | 101095665 A | 1/2008 |
| CN | 101632655 A | 1/2010 |
| CN | 102357226 A | 2/2012 |
| EP | 3187189 A1 | 7/2017 |
| JP | 2007131603 | 5/2007 |
| JP | 2007527418 | 9/2007 |
| JP | 2011132151 | 7/2011 |
| TW | 201006474 A | 2/2010 |
| TW | 201201794 A | 1/2012 |
| WO | WO2006087759 A2 | 8/2006 |
| WO | WO2007041276 A2 | 4/2007 |
| WO | WO2007112996 A2 | 10/2007 |
| WO | WO2010048114 A1 | 4/2010 |
| WO | WO2013100111 | 7/2013 |

OTHER PUBLICATIONS

Cadena et al, Nanoencapsulation of quercetin and resveratrol into elastic liposomes. Biochimica et biophysica acta, (Feb. 2013) vol. 1828, No. 2, pp. 309-316.*
Mohsen Meydani and Syeda T. Hasan, "Dietary Polyphenols and Obesity", nutrients, Jul. 8, 2010, p. 738-751, ISSN 2072-6643, www.mdpi.com/journal/nutrients.
Baba, "Prevalence of overweight and obesity among secondary school children (12-14yr) in the city of Mashhad, Iran", Clinical Biochemistry, vol. 44, No. 13, Suppl.p. S238-S239 on Jan. 29, 2018.
Israel Pérez-Torres et al., "Hibiscus Sabdariffa Linnaeus (Malvaceae), Curcumin and Resveratrol as Alternative Medicinal Agents Against Metabolic Syndrome", Received: Mar. 27, 2012 Revised: May 29, 2012 Accepted: Jun. 1, 2012, 2013, vol. 11, No. 1, pp. 25-37, Cardiovascular & Hematological Agents in Medicinal Chemistry.
Srujana Rayalam et al., "Resveratrol induces apoptosis and inhibits adipogenesis in 3T3-L1 adipocytesi", 2008, Received Aug. 22, 2007 Revise Nov. 29, 2007 Accepted Dec. 13, 2007, pp. 1367-1371, Phytotherapy Research.

(Continued)

*Primary Examiner* — Qiuwen Mi
(74) *Attorney, Agent, or Firm* — WPAT, PC

(57) ABSTRACT

Disclosed in the present invention is the composition for reducing local fat and body weight, and pharmaceuticals and use thereof. The composition contains resveratrol and curcumin extract at a weight ration from 1:30 to 10:1. The composition and pharmaceuticals thereof of the invention can inhibit the growth of fat cells, cause planned apoptosis of fat cells, achieve the effects of reducing fat cells, and reducing local fat deposition and body weight without causing inflammations or necrosis of surrounding cells or tissues and inflammations or pain reactions of surrounding tissues, thereby avoiding the problems of tissue damage and inflammatory pains caused by liposuction or low invasion fat-dissolving apparatus used in the prior art and the problems such as surrounding tissue inflammations and necrosis infections triggered by cell disruption and necrosis caused by components of a fat-dissolving injection, phosphatidylcholine or sodium deoxycholate.

20 Claims, 20 Drawing Sheets

(56) References Cited

OTHER PUBLICATIONS

Dong Young Rhyu et al., "[P8-142] Effects of Curcuma Longa MeOH Extract on Adipogenesis and Lipolysis in 3T3-L1 Adipocyle", Nov. 2009, pp. 347-347 (1 pages), The korean Society of Food Science and Nutrition.

Pabyton G. Cadena et al., "Nanoencapsulation of quercetin and resveratrol into elastic liposomes", 2013, pp. 309-316, Biochimica et Biophysica Acta 1828, Oct. 22, 2012, Elsevier B.V. All rights reserved.

\* cited by examiner

PLANT EXTRACT COMPOSITION FOR REDUCING TOPICAL FAT AND PROMOTING WEIGHT LOSS AS WELL AS APPLICATIONS THEREOF

FIELD OF THE INVENTION

The present invention relates to a composition, and more particularly to a composition used for reducing localized fat and reducing weight. The present invention relates to an application of the composition, and more particularly to the application used for reducing localized fat and reducing weight. The present invention further relates to a pharmaceutical composition comprising the composition, and more particularly to the pharmaceutical composition used for reducing localized fat and reducing weight. The present invention further relates to an application, and more particularly to the application of the pharmaceutical composition used for reducing localized fat and reducing weight.

BACKGROUND OF THE INVENTION

With more and more people's change on the concept of beauty, and the increasing standards in their personal health, body shape, and weight, weight loss and body contouring are no longer issues cared only by obese individuals. Therefore, weight loss and fitness center and weight management market are booming, driving relative developments such as, diet foods, fitness products, weight loss clinical management, medical equipment, fitness equipment, etc. According to the statistic report "Global Weight Loss and Gain Market 2009-2014" issued by Marketsand Markets, the global weight management market was estimated to be US $586.3 billion in 2014 and could grow into $650.9 billion in 2015; wherein the primary market is the United States, it's market scale was estimated to reach $310 billion, and the estimated market scale of Europe, the second largest market, is $238 billion. At the same time, due to the rise of consumer's concern of the awareness on health, especially on the after effects of chronic diseases caused by obesity, has made it an increasingly important agenda globally; therefore, besides targeting the obesity population, more and more people are actively developing on body weight control and body contouring for the healthy population, which has drawn strong attentions of all industries towards the body weight control and body contouring and led to the development boom in the industry, the above-mentioned reasons are all the main reasons why the market could grow steadily. The statistics of American Society of Plastic Surgeons (ASPS) issued in 2012 showed that the demand of body contouring has continuously ranked first in the field of plastic surgery and estimated demands would maintain an annual growth rate at about 12.3% until 2017. "Global Pipeline Analysis, Competitive Landscape and Market Forecasts" published by Research and Markets showed that global market of body contouring equipment reached $900 million in 2010 and estimated to increase into $2 billion in 2017. It is because the demand of the body contouring market is huge and keeps on growing every year, various ways of liposuction and lipolytic methods appear on the market. In contrast, many high-risk or unsafe medical treatments have also appeared one after another.

Conventional liposuction surgery was developed as early as in the 1970s; because of the way of liposuction by dry liposuction under negative pressure without any infusion solution, the subcutaneous nerves and blood vessels were damaged greatly; moreover, the amount of blood loss was large and the risk of surgery was high. Tumescent liposuction and super wet liposuction were developed later on. Tumescent liposuction is by adding anesthetic and vasoconstrictor into the infusion solution, even though, in this method, local anesthesia replaces intravenous anesthesia, large amount of infusion solution has caused the anesthetic requires at least 12 hours to be metabolized, and hence increased the possible risks of local anesthetic to human body. Recently, the method which doctors preferably choose to use on large amount of liposuction is super wet liposuction, its characteristic is that the volume exchange of infusion solution has to be equal to the extracted fat and the chance of overload infusion can be effectively reduced. However, clinically, there are limitations to the sites of administration, the sites are primarily the areas with large fat accumulation such as the abdomen, and the thighs etc; meanwhile, the efficacy and safety of liposuction depend entirely on the skill and the proficiency of the surgeon. The process of liposuction cause much harm to the body, time-consuming, and would still causes side effects such as, severe postoperative bruising, swelling, pain and sensory paralysis, scar tissue, unsmooth skin surface; the recovery period could range from four to six weeks. Due to the lengthy operation time of liposuction, the greater blood loss has directly increased its surgical risk. Therefore, various auxiliary liposuction instruments are being designed by every industry, and thus auxiliary methods of liposuction like ultrasound and laser were developed one after another, the key factor is still the skill of the performing surgeon. Furthermore, cases of tissue burn or poor efficacy occur frequently while using relative auxiliary liposuction instruments. In view of the drawback faced in liposuction, every industry was continuously making improvements in both technique and instrument; the aesthetic medical industry of the United States and Europe are focusing on the development of aesthetic medical equipment since the 1980s. In the field of body weight control and body contouring, the manufacturers have transformed their main appeal from traditional liposuction to minimally invasive and even non-invasive lipolysis instrument. The goals of lipolytic products or instruments are to improve the traditional faults of large blood loss, lengthy recovery period, postoperative scars, and try to be less invasive, high safety, convenient, smaller wound, and short recovery period as possible; at the same time, maintain the advantages of better efficacy and competitive price for it to enter the aesthetic medical market with the enough advantages.

There is a lipolytic method by using mesotherapy, which uses phosphatidylcholine or sodium deoxycholate as active ingredients to inject to the obese region to lyse fat. The structure of this kind of ingredients is similar to the ingredient of cell membrane; therefore, it could break down the cell membrane of adipocyte cells and trigger cell necrosis. Injecting this kind of medicine into the mesoderm would cause massive adipocyte cell necrosis and then cause fat release; due to the medicine does not possess specificity, namely, not only targeted on adipocytes, many normal surrounding cells would also be affected and thus cause necrosis, in addition, cell necrosis would cause the surrounding tissue to initiate a series of inflammation reaction, further causing administration site inflammation, severe pain, and swelling, and even causing the risks of local tissue necrosis or infection. Although lipolytic method by injection, comparing to using large liposuction instrument, could overcomes the limitation in administration site, one lipolysis injection treatment course may require several dozens of injections every 2 weeks and 1 to 6 treatment course(s) to reach the goal of lipolysis effect. Although anesthetic has been added to the injection solution, the injected site may still suffer from severe inflammation and pain after the anesthesia has subsided, in addition, the number of treatment and injection frequency also needs to be improved. Consider of the risks of severe postoperative pain, nerve paralysis, local tissue necrosis, or infections, the limited dosage in single injection, and restricted to be applied in face, most surgeons no longer inject the ingredients mentioned above to reduce localized fat of the patient; although the United States has approved the first lipolysis inject product made from sodium deoxycholate, it has a certain degree of side-effects and could only use in double chin, making its usage to be limited. Overall, a product that could effectively reduce localized fat, has lower side effects, safer is lacking on the current market; therefore, under the high demand of surgeons and consumers, it is a trend in the market to develop a localized lipolysis injection formulation that is safer, with low side effects, and could overcome the mentioned defects and limitations.

SUMMARY OF THE INVENTION

The present invention provides a composition used for reducing localized fat and reducing weight, comprising a weight ratio of resveratrol to turmeric extract ranging from 1:50 to 15:1. Preferably, the weight ratio of resveratrol to turmeric extract ranging from 1:50 to 10:1. Preferably, the weight ratio of resveratrol to turmeric extract ranging from 1:30 to 10:1. Preferably, the weight ratio of resveratrol to turmeric extract ranging from 1:50 to 2:1. Preferably, the weight ratio of resveratrol to turmeric extract is 1:19.

The present invention provides a composition used for reducing localized fat and reducing weight, comprising a weight ratio of resveratrol to curcumin ranging from 1:50 to 15:1. Preferably, the weight ratio of resveratrol to curcumin ranging from 1:50 to 10:1. Preferably, the weight ratio of resveratrol to curcumin ranging from 1:30 to 10:1. Preferably, the weight ratio of resveratrol to curcumin ranging from 1:50 to 2:1. Preferably, the weight ratio of resveratrol to curcumin is 1:19.

The composition of the present invention can inhibit adipocytes growth and induce planned adipocyte apoptosis to reach the effect of reducing localized fat deposits and decreasing adipocytes; it can also reduce body weight but does not cause the surrounding cells and the tissue inflammation or tissue necrosis, nor would it cause inflammation or severe pain to the surrounding tissues, thus avoids the tissue damage, inflammation, and pain caused by above mentioned liposuction surgery or low-invasive lipolysis instrument. Moreover, it would not cause necrosis nor result in problems such as surrounding tissue inflammation or infection in the surrounding tissues as triggered by necrosis caused by lipolysis injection composition ingredient phosphatidylcholine or sodium deoxycholate. The present invention can reduce weight as well.

According to the present invention, the term "turmeric extract" as used herein refers to the extract comprises curcumin, wherein the turmeric extract comprises 80% to 100% of curcumin.

In the present invention, when the concentration of drugs (i.e., resveratrol or curcumin) expressed as mg/mL, it indicates the amount of milligrams of drugs per milliliter of solution.

In the present invention, the term "micelle" refers to a microstructure formed by surfactants, wherein each of the surfactants has a hydrophilic end and a hydrophobic (lipophilic) end, and the surfactants are arranged in a way that the hydrophilic ends face outward and the hydrophobic (lipophilic) ends face inward to form the microstructure. Preferably, the microstructure is a spherical structure, a spheroidal structure, or other microstructural structures.

Preferably, the composition of the present invention further comprises drug-containing micelles, wherein the drug-containing micelles are the micelles containing curcuminoid. Preferably, drug-containing micelles are the micelles containing curcumin. Preferably, drug-containing micelles are the micelles encapsulating or containing curcuminoid. Preferably, drug-containing micelles are the micelles encapsulating or containing curcumin.

Preferably, the composition of the present invention further comprises second lipophilic drug-containing micelles, wherein the second lipophilic drug-containing micelles are the micelles containing any lipophilic drug except curcuminoid. Preferably, the second lipophilic drug-containing micelles are the micelles encapsulating or containing the second lipophilic drug.

Wherein, the term "any lipophilic drug except curcuminoid" refers to at least one of quercetin, synephrine, puerarin, resveratrol, and any lipophilic drug except curcuminoid, or combination thereof. Or, "any lipophilic drug except curcuminoid" refers to any lipophilic drug except curcumin.

In the present invention, the composition comprising drug-containing micelles or/and second lipophilic drug-containing micelles has better weight loss effect than the composition without drug-containing micelles and second lipophilic drug-containing micelles.

The present invention also provides a preparation method of a composition comprising resveratrol and turmeric extract. The method comprises: mixing a composition with at least one of the pharmaceutically acceptable salts composition, pharmaceutically acceptable stabilizers or bacteriostatic agents or pharmaceutically acceptable emulsifiers, excipient such as surfactants, anesthetics, wherein the composition comprises resveratrol and turmeric extract; and preparing the mixture into an injection formulation.

Preferably, the stabilizer comprises, but is not limited to, xylitol, sorbitol, polydextrose, isomalt or dextrose.

Preferably, the "pharmaceutically acceptable excipient" comprises, but is not limited to, lubricant, suspending agent, solubilizer, glidant, emulsifier or surfactant. The quantity of excipient required will depend upon the quantity of the active ingredient, and one excipient can perform one or more functions.

Preferably, the lubricant comprises but are not limited to, agar, calcium stearate, ethyl oleate, ethyl laurate, glycerin, glyceryl palmitostearate, hydrogenated vegetable oil, magnesium oxide, magnesium stearate, mannitol, poloxamer, ethylene glycol, sodium benzoate, sodium lauryl sulfate, sodium stearoyl acid, sorbitol, stearic acid, talc, or zinc stearate.

Preferably, the suspending agent comprises, but are not limited to, mannitol, carboxymethyl cellulose (CMC), CMC-Na.

Preferably, the solubilizer comprises, but are not limited to, hydroxypropyl-beta-cyclodextrin, tween 80, or castor oil.

Preferably, the glidant comprises, but are not limited to materials such as magnesium stearate, silicon dioxide, magnesium trisilicate, powdered cellulose, starch, talc, tribasic calcium phosphate, calcium silicate, magnesium silicate, Colloidal Silicon Dioxide, silicon hydrogel, etc.

Preferably, the emulsifier might be a naturally occurring phospholipid, comprising, but not limited to, soybean lecithin, lecithin, monoglycerides, diglycerides, sodium stearate, sorbitan esters of fatty acid, or polyoxyethylene sorbitan monooleate.

Preferably, the surfactant comprises, but are not limited to, Tween, polyethylene-polypropylene glycol, polyoxyethylene-monostearate, polyoxyethylene alkyl ethers (e.g. polyoxyethylene lauryl ether), Triton-X, polyoxyethylene-polyoxypropylene copolymer, or sodium dodecyl sulfate (SDS).

Preferably, the hydrophilic-lipophilic balance value (HLB value) of the surfactant is greater than 10.

Preferably, the surfactant comprises, but are not limited to, a non-ionic surfactant.

Preferably, the non-ionic surfactant comprises, but are not limited to, at least one of polysorbate 80 (tween 80), propylene glycol, polyethylene glycol 600, 2-hydroxyethyl 12-hydroxyoctadecanoate (solutol HS 15), polyoxyethylene castor oil derivatives, and other non-ionic surfactants, or combination thereof.

Preferably, the polyoxyethylene castor oil derivatives comprises, but are not limited to, at least one of Kolliphor ELP (also known as cremophor ELP), cremophor RH 40, and other polyoxyethylene castor oil derivatives, or combination thereof.

The present invention further provides an application of the composition in preparing a pharmaceutical composition which is used for reducing localized fat and reducing weight.

The present invention further provides a pharmaceutical composition used to reduce localized fat and reduce weight; wherein, the pharmaceutical composition comprising an effective dosage of the composition which is used for reducing localized fat and reducing weight and a pharmaceutically acceptable carrier.

The pharmaceutical composition of the present invention can exist in multiple forms, including, but not limited to, liquid, semi-solid and solid pharmaceutical forms. For example, liquid solutions (e.g. injectable and infusible solution), dispersions, suspensions, powders, lyophilized powders, or liposomes or transdermal ointment or patch. The preferred form depends on the expected mode of administration and therapeutic application. Preferably, the pharmaceutical composition of the present invention is in the form of infusible solutions, and the preferred administration mode is non-intestinal mode, such as injectable solution. In an embodiment of the present invention, the pharmaceutical composition comprises an effective dosage of resveratrol and turmeric extract composition for reducing localized fat is subcutaneously administered. Preferably, the pharmaceutical composition comprising an effective dosage of resveratrol and turmeric extract composition for reducing localized fat is administered to subcutaneous fat by subcutaneous injection. In an embodiment of the present invention, the formulation of the ointment is well known in the art, including, but not limited to, active agent, wax, water, petrolatum, preservatives, higher alcohols, polyhydric alcohols, emulsifiers, solvents, thickeners, plasticizers, fragrances, buffers, antibiotics, stabilizers or mixtures thereof.

The dosage of the pharmaceutical composition of the present invention can be adjusted accordingly to different parameters. The parameters include, but are not limited to the type of the subject, the weight of the subject, and the thickness and area of the localized fat of the subject. The pharmaceutical composition of the present invention can be administered once, multiple or continuously within 24 hours, and can also be administered multiple or continuously per week or per month. The method of administration is by injection, subcutaneous implantation, implantable infusion, ointment, or patch. Preferably, the method of injection includes, but is not limited to subcutaneous injection, subcutaneous implantation, intravenous drip, intravenous infusion pump method, implantable infusion pump method.

The present invention further provides an application of the pharmaceutical composition used for reducing localized fat and reducing weight, which comprises administering an effective dosage of the pharmaceutical composition comprising resveratrol and turmeric extract composition to a local sites of a subject, to make the local site of the subject achieve the effect of inhibit adipocyte growth, promote adipocyte apoptosis, decrease fat deposition, and reduce weight.

Preferably, the subjects are human or animals.

Preferably, the effective dosage of the pharmaceutical composition to be administered to the subject every time is from 0.4 mg/kg to 100 mg/kg. More preferably, the effective dosage of the pharmaceutical composition to be administered to the subject every time is from 1 mg/kg to 60 mg/kg.

Preferably, the term "reduce body weight" as used herein refers to the reduction of body weight gain of the subject by 5% to 30%.

According to the present invention, the term "reducing localized fat" as used herein refers to: after administering the effective dosage of compositions comprising resveratrol and turmeric extract of the present invention, adipocyte growth could be inhibited, adipocytes initiate procedural or planned apoptosis, and the localized deposit fat could be reduced. As shown in the embodiment of the present invention, the amount of localized fat reduction can be detected by administering a specific range of the dosage of the composition comprising resveratrol and turmeric extract, and measuring the growth inhibitory rate of adipocytes, cell apoptosis degree, and the change of the subcutaneous fat and visceral fat of rats in a specific period. Preferably, the localized fat includes, but is not limited to, subcutaneous fat, visceral fat, localized deposit fat, or adipocytes.

Preferably, the localized fat sites include, but are not limited to, face, jaw, arm, waist, abdomen or thighs.

The effect of the composition or the pharmaceutical composition of the present invention is significantly superior to that of resveratrol or turmeric extracts administered alone. Moreover, there has never been a precedent of resveratrol or turmeric extracts administered alone, or together, to reduce localized fat by localized injection. Furthermore, the present invention is primarily to inhibit adipocyte growth and promote adipocyte apoptosis to reduce localized fat by administrating medicine through localized injection, without affecting surrounding cells or tissues, and no significant side effect was found in animal assay. Therefore, the composition or the pharmaceutical composition of the present invention is safer with fewer side effects. The technical level of the composition or the pharmaceutical composition in the present invention is completely different from existing techniques or products. Thus, it could be used to avoid the problems of localized cells necrosis, severe pain, inflammation and necrosis and/or infection of surrounding tissues caused by conventional liposuction surgery, lipolysis instruments such as high-intensity focused ultrasound lipolysis instrument, or lipolytic injection ingredients such as phosphatidylcholine and sodium deoxycholate. Moreover, it can also significantly reduce postoperative bruising, swelling, pain and sensory paralysis, as well as shorten recovery period of the patient.

DETAILED DESCRIPTION OF THE INVENTION

The technical means, accompanied by the drawings and the preferred embodiments of the present invention, taken to achieve the projected invention purpose could be further elaborated below.

Embodiment 1: Preadipocyte Growth Inhibition Assay

In this embodiment, 3T3-L1 preadipocytes were incubated in 96-well plates with $1 \times 10^4$ cells per well. With the exception of the DMSO solution control group (control group), 50 ppm resveratrol, 50 ppm turmeric extract, 80 ppm green tea extract, and 100 ppm of the composition UL003A, UL003C, or UL003R in the present invention were added into different wells respectively. There were seven groups and three replicates were preformed in each group. After administration process and 48 hours incubation, photos were taken to record the cell's growth condition, and the growth inhibitory effect of 3T3-L1 preadipocytes in each group was analyzed by MTT assay. In composition UL003A, the weight ratio of resveratrol to green tea extract is 9:1; in the composition UL003C, the weight ratio of resveratrol to turmeric extract is 1:19; in the composition UL003R, the weight ratio of resveratrol to turmeric extract is 9:1. Data of all groups are presented in Mean±SD. The letters a, b, c, d, and e represent the results of the statistics. Different letters represent statistical difference among the groups (p<0.05).

Figure 1:
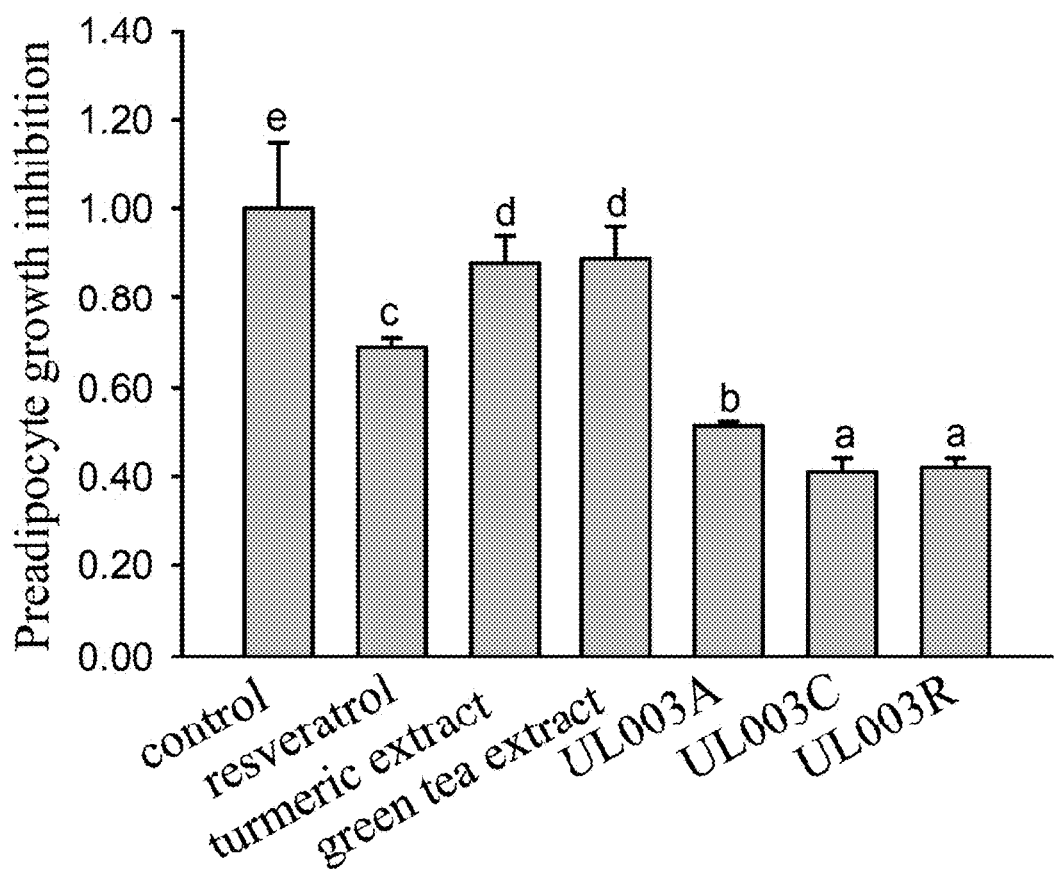
FIG. 1 is the bar chart presenting the effect of inhibiting preadipocytes growth in each group tested by MTT assay in the present invention.

Results are shown as in FIG. 1, compared to the DMSO solvent control group, the compositions UL003A, UL003C, and UL003R of the present invention could all effectively inhibit preadipocytes growth (p<0.05); compared to the single plant extracts groups, the compositions UL003A, UL003C, and UL003R had better inhibitory effect, and the differences are significant (p<0.05).

Embodiment 2: Differentiating Adipocytes Growth Inhibition Assay

In this embodiment, 3T3-L1 preadipocytes cells were incubated in 12-well plates with $1 \times 10^5$ cells per well. The medium was replaced with medium containing 5 μg/ml of insulin differentiation agent, 1 μM of dexamethasone, 0.5 mM of 3-isobutyl-1-methylxanthine on the fourth day of incubation. DMSO, 50 ppm of resveratrol, 50 ppm of turmeric extract, 80 ppm of green tea extract, and 100 ppm of the composition UL003A, UL003C, or UL003R in the present invention were add to different wells respectively, wherein the group added with DMSO was control group. There were seven groups and three replicates were performed in each group. After administration process and 48 hours incubation, photos were taken to record the cell's growth condition, and the inhibitory effect of respective experimental matters on the differentiating adipocytes was analyzed by MTT assay. Data of all groups are presented in Mean±SD. The letters a, b, c, d, e, and f represent the results of the statistics. Different letters represent statistical difference among groups (p<0.05).

Figure 2:
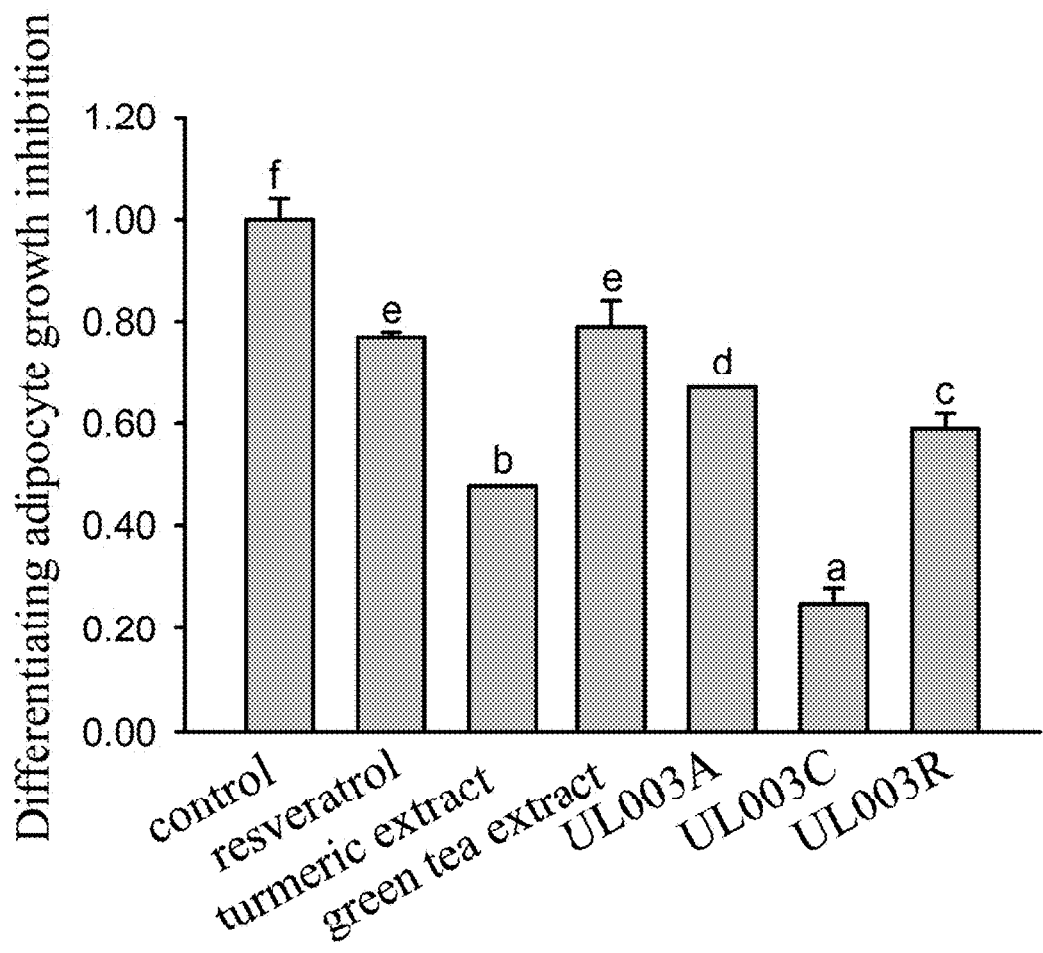
FIG. 2 is the bar chart presenting the effect of inhibiting differentiating adipocytes growth in each group tested by MTT assay in the present invention.

Results are shown as in FIG. 2, compared to the DMSO solvent control group, all of the compositions UL003A, UL003C, and UL003R of the present invention could significantly inhibit differentiating adipocytes growth (p<0.05), wherein the composition UL003C had the best inhibitory effect on differentiating adipocytes growth. Compared to other single plant extract groups, the composition UL003C had better inhibitory effect on differentiating adipocyte growth. (p<0.05).

Embodiment 3: Mature Adipocytes Growth Inhibition Assay

In this embodiment, the inhibitory effect of the composition of the present invention on mature localized adipocytes is compared with the inhibiting effect of the conventional sodium deoxycholate. In this embodiment, 3T3-L1 cells were incubated in 12-well plates with $3 \times 10^4$ cells per well. The medium was replaced with an incubation fluid containing 5 μg/ml of insulin, 1 μM of dexamethasone, and 0.5 mM of 3-isobutyl-1-methylxanthine on the fourth day of incubation. After incubation for another two days, medium was renewed with an incubation fluid containing 5 μg/ml insulin to incubate for additional four days. When 3T3-L1 cell differentiation was completed, with the exception of the PBS solvent control group and the DMSO solvent control group, 50 ppm or 100 ppm of the composition UL003C or sodium deoxycholate were added to different wells respectively. There were six groups and three replicates were performed in each group. After administration process and 48 hours incubation, photos were taken to record the cell's growth condition, and the inhibitory effect of respective experimental matters on mature adipocytes was analyzed by MTT assay.

Figure 3:
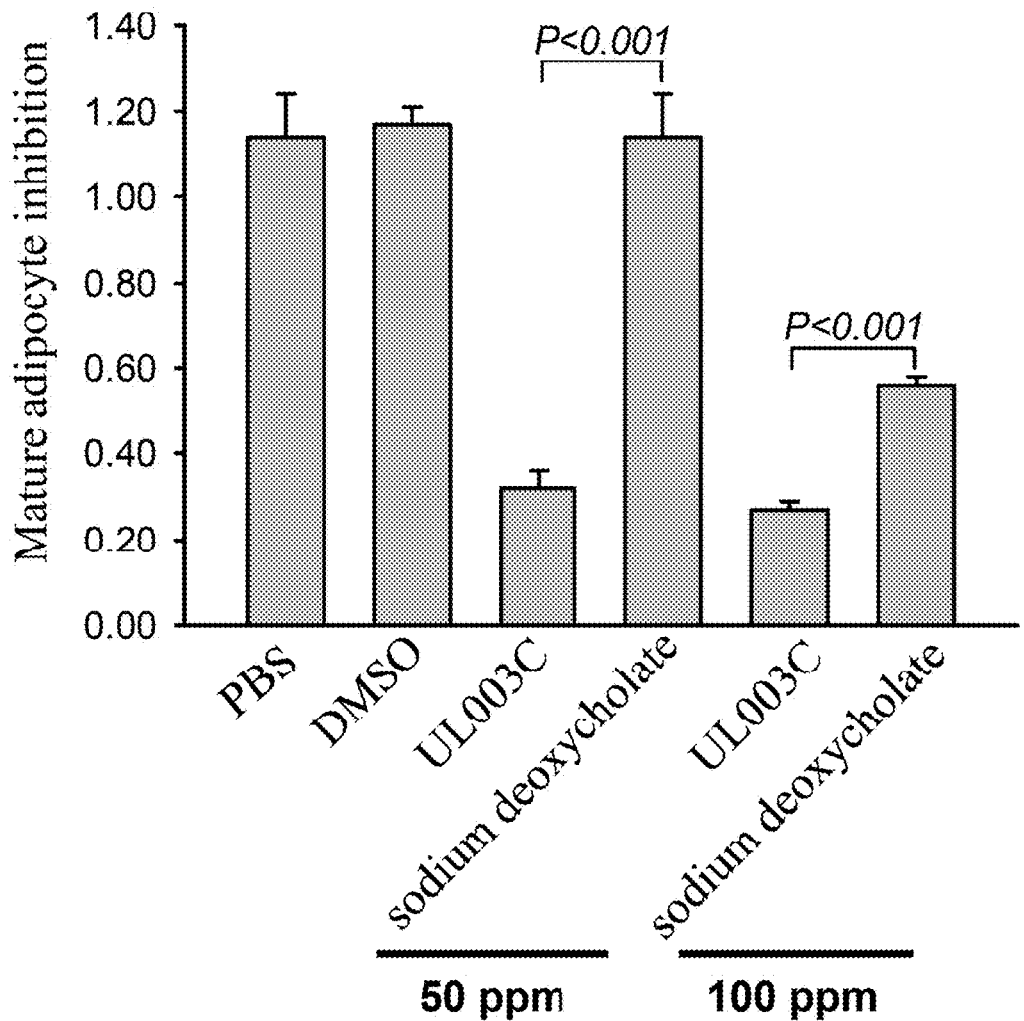
FIG. 3 is the bar chart presenting the effect of the formulation UL003C and sodium deoxycholate on mature adipocytes growth inhibition tested by MTT assay in the present invention.

Results are shown as in FIG. 3, the composition of the present invention could effectively inhibit mature adipocytes growth; at both of the two different dosages of 50 ppm and 100 ppm, the inhibitory effect of the composition UL0003C of the present invention on mature adipocytes was significantly greater than that of sodium deoxycholate (p<0.001).

Embodiment 4: Adipocyte Apoptosis Assay (I)

In this embodiment, 3T3-L1 cells were incubated in 12-well plates with $1 \times 10^5$ cells per well. The medium was replaced with an incubation fluid containing 5 μg/ml of insulin differentiation agent, 1 μM of dexamethasone, and 0.5 mM of 3-isobutyl-1-methylxanthine on the fourth day of incubation. After culturing the cells for four days in the incubation fluid containing differentiation agent and waiting until the adipocyte differentiation has been completed, with the exception of the DMSO solvent control group, 50 ppm of compositions UL003A, UL003C, and UL003R of the present invention were added to different wells respectively. There were four groups and three replicates were performed in each group. After administration process and 24 hours incubation, cells were collected and then stained with Annexin V/PI, and cell apoptosis was analyzed by flow cytometer; wherein Annexin V–PI– represents the number of survival mature adipocytes, and Annexin V+PI+ represents the number of apoptotic mature adipocytes; this method is used to distinguish and determine the apoptosis degree induced by the experimental matters in each group.

Figure 4:
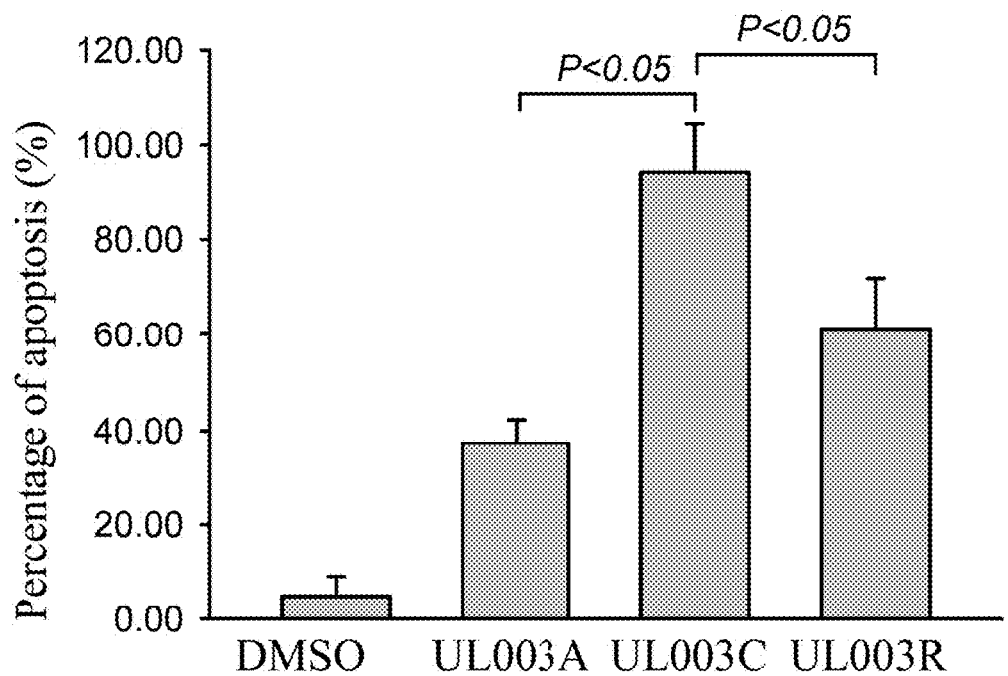
FIG. 4 is the bar chart presenting the effect of the formulations UL003A, UL003C and UL003R on adipocyte apoptosis promotion in the present invention obtained by labeling with Annexin V/PI and then detecting with flow cytometer.

Results are shown as in FIG. 4, after treating the mature adipocytes with the above mentioned experimental matters for 24 hours, all of the compositions UL003A, UL003C, and UL003R of the present invention could significantly induced mature adipocytes apoptosis (p<0.05) compared to the DMSO solvent control group, wherein composition UL003C has the best apoptotic effect on mature adipocytes which is significantly better than composition UL003A and UL003R (p<0.05).

Embodiment 5: Adipocyte Apoptosis Assay (II)

In this embodiment, 3T3-L1 cells were incubated in 12-well plates with $1 \times 10^5$ cells per well. The medium was replaced with an incubation fluid containing 5 μg/ml of insulin differentiation agent, 1 μM of dexamethasone, and 0.5 mM of 3-isobutyl-1-methylxanthine on the fourth day of incubation. After four days incubation in the incubation fluid containing differentiation agent and waiting until the adipocytes have matured, with the exception of the DMSO solvent control group, 50 ppm and 100 ppm of the compositions UL003A, UL003C, and UL003R of the present invention were respectively added to different wells. There were seven groups and three replicates were performed in each group. After administration process and 3 hours incubation, cells were collected and the caspase 3 stain was performed. Cell apoptosis was analyzed by flow cytometry, wherein if the caspase 3 of the cells have been labeled, it represents the cells initiated apoptosis; this method is used to compare the apoptosis degree induced by the experimental matters in each group under different dosage.

Figure 5:
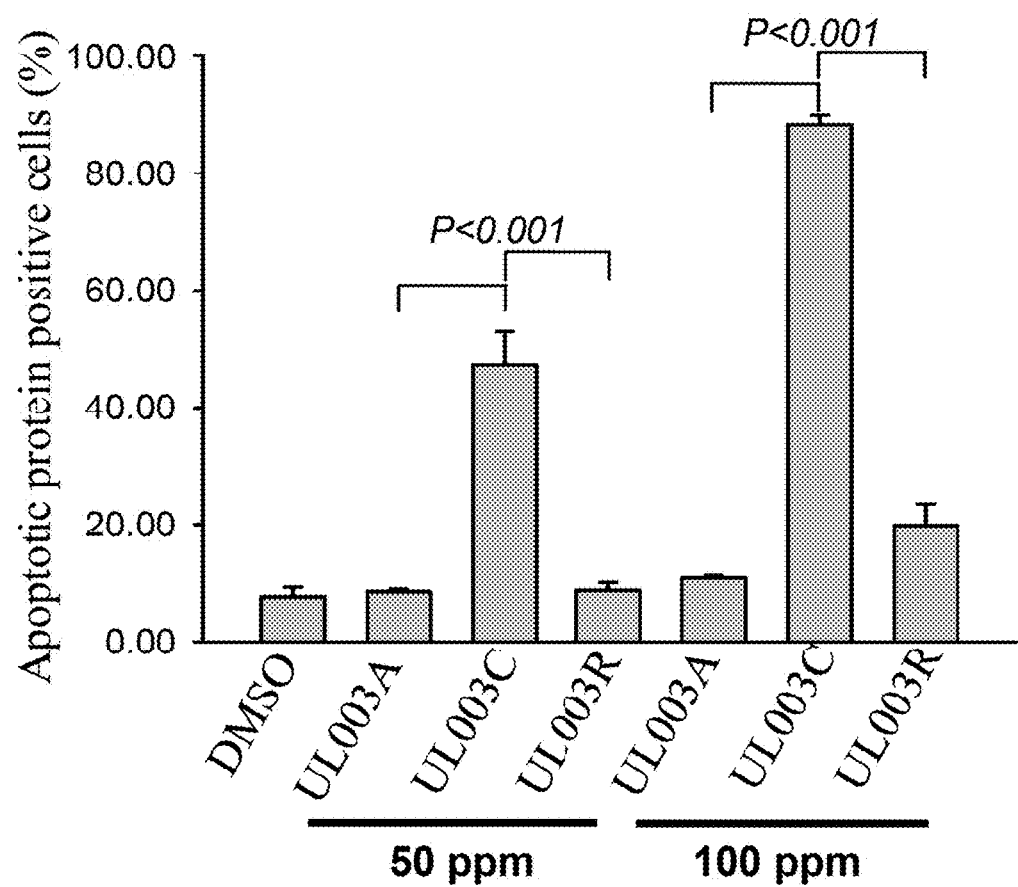
FIG. 5 is the bar chart presenting the effect of the formulations UL003A, UL003C and UL003R on adipocyte apoptosis promotion in the present invention obtained by performing caspase 3 stain and then detecting with flow cytometer.

Results are shown as in FIG. 5, compared to the DMSO solvent control group, no matter the mature adipocytes were treated with 50 ppm or 100 ppm of composition UL003C of the present invention, caspase 3-labeled cells in these groups were significantly more than that in the DMSO solvent control group (p<0.001). It indicates that the composition UL003C could significantly induce mature adipocytes apoptosis, and has the best effect.

Embodiment 6: Adipocyte Apoptosis Assay (III)

In this embodiment, 3T3-L1 cells were incubated in 12-well plates with $1 \times 10^5$ cells per well. The medium was replaced with an incubation fluid containing 5 µg/ml of insulin differentiation agent, 1 µM of dexamethasone, and 0.5 mM of 3-isobutyl-1-methylxanthine on the fourth day of incubation. After four days incubation in the incubation fluid containing differentiation agent and waiting until the adipocytes have matured, with the exception of the DMSO solvent control group, 50 ppm turmeric extract, 50 ppm resveratrol, and ppm and 100 ppm of the composition UL003C in the present invention was added to each group respectively to perform the experiment; there were five groups and three replicates were performed in each group. According to previously published articles, cells treated with resveratrol for 16 hours were more likely to be labeled by caspase 3, cells in the remaining groups were treated with medicine and incubated for 3 hours. Cells were collected and perform caspase 3 stain, and cell apoptosis was analyzed by flow cytometry. Cells with labeled-caspase 3 represents the number of apoptotic cells; this method is used to compare the apoptosis degree induced by the experimental matters in each group under different dosage.

Figure 6:
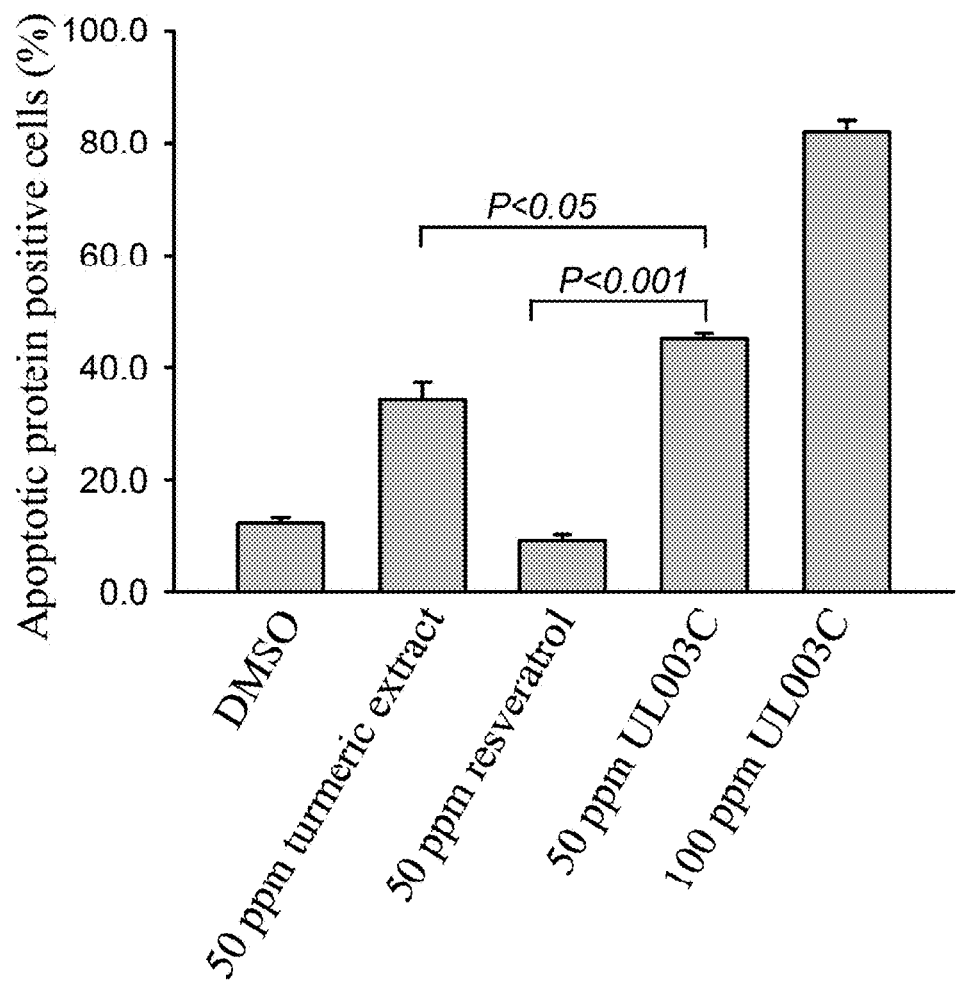
FIG. 6 is the bar chart presenting the effect of turmeric extract, resveratrol and the formulation UL003C on adipocyte apoptosis promotion in the present invention obtained by performing caspase 3 stain and then detecting with flow cytometer.

Results are shown as in FIG. 6, after adipocytes were treated with 50 ppm of composition UL003C of the present invention, cells with labeled caspase 3 in these group were significantly more than that in the DMSO solvent control group, (p<0.001) and also significantly more than the turmeric extract group (p<0.05) and resveratrol group (p<0.001) with the same dosage. It indicates that the effect of the composition UL003C in the present invention on promoting mature adipocytes apoptosis is significantly superior to the effect of any single one plant extract ingredient in the composition.

Embodiment 7: Adipocyte Apoptosis Assay (IV)

In this embodiment, the effect of composition UL003C in the present invention on mature adipocytes apoptosis promotion was compared with that of the well-known sodium deoxycholate. In this embodiment, 3T3-L1 cells were incubated in 12-well plates with $1 \times 10^5$ cells per well. The medium was replaced with an incubation fluid containing 5 µg/ml of insulin differentiation agent, 1 µM of dexamethasone, and 0.5 mM of 3-isobutyl-1-methylxanthine on the fourth day of incubation. After four days incubation in the incubation fluid containing differentiation agent and waiting until the adipocyte cells matures, with the exception of the DMSO solvent control group, 100 ppm of composition UL003C and sodium deoxycholate were added to different wells respectively; there are three groups in the experiment, and three replicates were performed in each group. After administration process and 24 hours incubation, cells were collected and Annexin V/PI stain was performed. Cell apoptosis was analyzed by flow cytometry, wherein Annexin V−PI− cells represented the number of the survival mature adipocytes, and Annexin V+PI+ cells represented the number of the apoptotic mature adipocytes; this method is used to compare the apoptosis degree induced by the experimental matters in the two groups.

Figure 7:
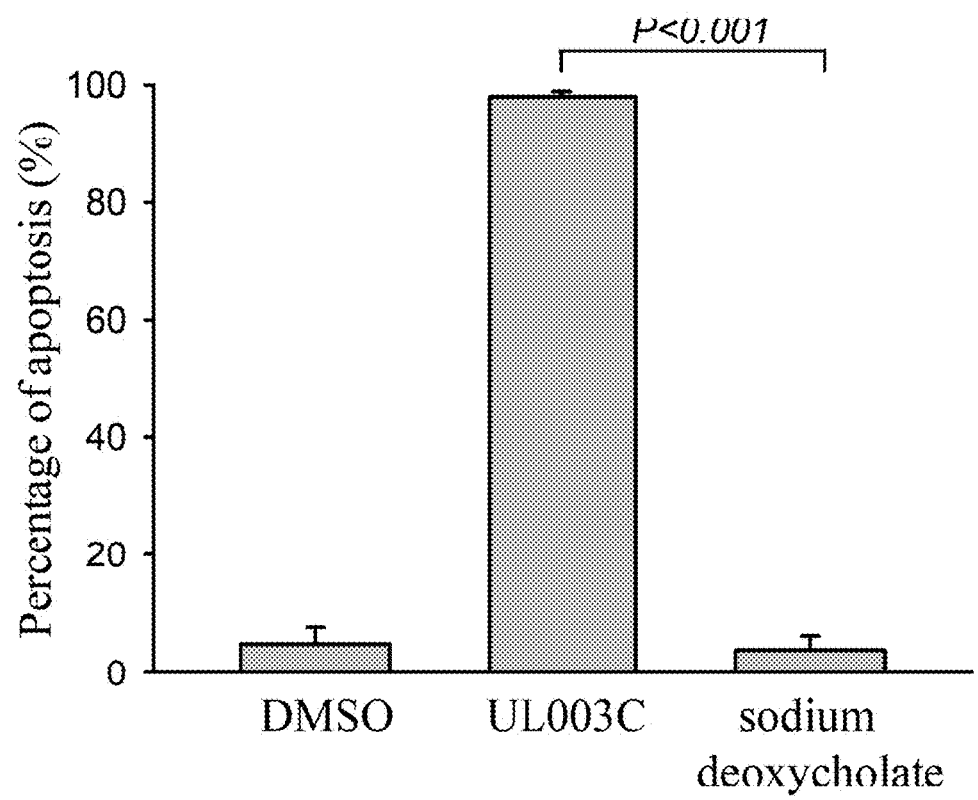
FIG. 7 is the bar chart presenting the effect of the formulation UL003C and sodium deoxycholate on adipocyte apoptosis promotion in the present invention obtained by labeling with Annexin V/PI and then detecting with flow cytometer.

Results are, shown as in FIG. 7, compared to the DMSO solvent control group and sodium deoxycholate with the same concentration, the composition UL003C could significantly induce mature adipocytes apoptosis (p<0.001). In contrast, there was no significant difference between the DMSO solvent control group and sodium deoxycholate group (p>0.05). It indicates that composition UL003C in the present invention could significantly induce mature adipocytes apoptosis, and the known locally lipolytic ingredient sodium deoxycholate does not.

Embodiment 8: Adipocyte Apoptosis Assay (V)

In this embodiment, the effect of various compositions comprising resveratrol and curcumin on mature adipocytes apoptosis promotion were compared with that of resveratrol or curcumin.

3T3-L1 cells were incubated in 12-well plates with $1 \times 10^5$ cells per well. The medium was replaced with a DMI medium containing 5 µg/ml of insulin, 0.1 µM of dexamethasone, and 0.5 mM of 3-isobutyl-1-methylxanthine (referred as IBMX) on the third day of incubation. After seven days incubation in the medium containing differentiation agent and waiting until the adipocyte cells matures, with the exception of the DMSO solvent control group, 50 ppm of curcumin, resveratrol, composition UL003C6, composition UL003C5, composition UL003C4, composition UL003C3, composition UL003C2, composition UL003C1, composition UL003B, composition UL003R1, composition UL003R2, and composition UL003R3 were added to different wells respectively; there are 13 groups in the experiment, and four replicates were performed in each group.

Please refer to Table 1, which presents the experimental matters and their final concentration in each group. The ratios of resveratrol to curcumin (weight ratio) in the UL003C6 group, UL003C5 group, UL003C4 group, UL003C3 group, UL003C2 group, UL003C1 group, UL003B group, UL003R1 group, UL003R2 group, and UL003R3 group were 1:50, 1:40, 1:20, 1:10, 1:5, 1:2, 1:1, 2:1, 5:1, and 15:1, respectively, and the final concentration of the sum of resveratrol and curcumin in each of these groups was 50 ppm. The final concentration of resveratrol in the resveratrol group was 50 ppm, and the final concentration of curcumin in the curcumin group was 50 ppm.

After administration process and 24 hours incubation, cells were collected and Annexin V/PI stain was performed. Cell apoptosis was analyzed by flow cytometry, wherein Annexin V−PI− cells represented the number of the survival mature adipocytes, and Annexin V+PI+ cells represented the number of the apoptotic mature adipocytes; this method is used to compare the apoptosis degree induced by the experimental matters in each group.

Figure 8:
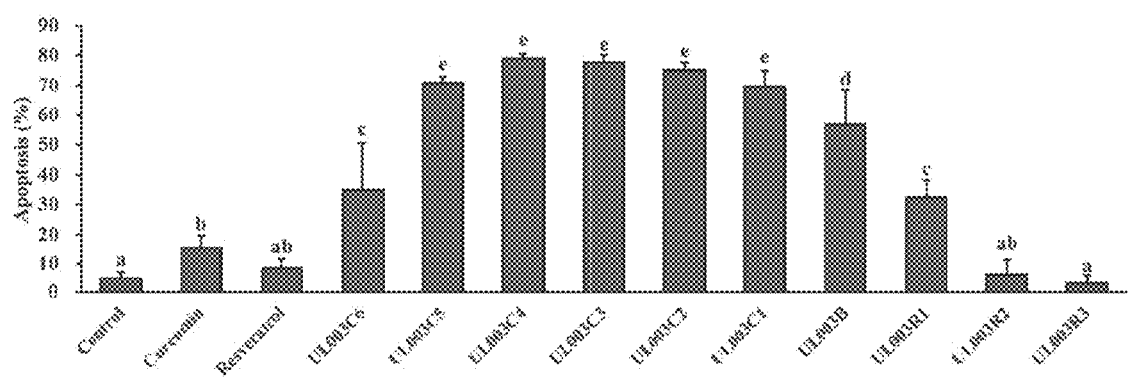
FIG. 8 is the bar chart presenting the effect of the various complex pharmaceutical compositions on adipocyte apoptosis promotion in the present invention obtained by labeling with Annexin V/PI and then detecting with flow cytometer.

Results are shown as in FIG. 8, the percentage of apoptotic cells of the DMSO solvent control group was 5.14±2.05%, the percentage of apoptotic cells of the curcumin group was 15.43±4.31%, the percentage of apoptotic cells of the resveratrol group was 8.48±3.23%, the percentage of apoptotic cells of the UL003C6 group was 34.95±15.73%, the percentage of apoptotic cells of the UL003C5 group was 70.73±2.18%, the percentage of apoptotic cells of the UL003C4 group was 78.99±1.78%, the percentage of apoptotic cells of the UL003C3 group was 77.52±2.59%, the percentage of apoptotic cells of the UL003C2 group was 75.29±2.34%, the percentage of apoptotic cells of the UL003C1 group was 69.64±5.33%, the percentage of apoptotic cells of the UL003B group was 56.92±11.74%, the percentage of apoptotic cells of the UL003R1 group was 32.56±5.73%, the percentage of apoptotic cells of the UL003R2 group was 6.38±5.06%, the percentage of apoptotic cells of the UL003R3 group was 3.06±3.03%.

Compared to the DMSO solvent control group, curcumin group, and resveratrol group, all of the composition UL003C6, UL003C5, UL003C4, UL003C3, UL003C2, UL003C1, UL003B, and UL003R1 could significantly induce mature adipocytes apoptosis (p<0.05). It indicates that curcumin and resveratrol in the these compositions have synergistic effect in the efficacy of adipocyte apoptosis, wherein composition UL003C5, UL003C4, UL003C3, UL003C2, UL003C1 have a much better apoptotic effect on mature adipocytes.

Embodiment 9: The Effect of Complex Pharmaceutical Composition with Excipient on the Subcutaneous Fat of Rats A curcumin-resveratrol complex solution without excipient, a curcumin-resveratrol complex solution comprising HS 15, and a curcumin-resveratrol complex solution comprising ELP were prepared as follows:

Preparation of the curcumin-resveratrol complex solution comprising ELP:
  0.05 g of resveratrol, 0.95 g of curcumin, and 150~200 mL of dichloromethane were mixed together, and stirred at 150~500 rpm at room temperature until curcumin dissolved completely. 40 g of Kolliphor ELP (also known as Cremophor ELP, abbreviated as ELP) was added and stirred at 100~300 rpm to volatilize dichloromethane. Once dichloromethane volatilized completely, normal saline for injection was slowly added to a total volume of 200 mL. The solution was mixed well to obtain a curcumin-resveratrol complex solution comprising ELP. The concentration of Kolliphor ELP (ELP) was approximately 20% (v/v), the weight ratio of resveratrol to curcumin was 1:19, and the concentration of the sum of resveratrol and curcumin was 5 mg/mL.

Preparation of the curcumin-resveratrol complex solution comprising HS 15:
  0.05 g of resveratrol, 0.95 g of curcumin, and 150~200 mL of dichloromethane were mixed together, and stirred at 150~500 rpm at room temperature until curcumin dissolved completely. 40 g of solutol HS 15 was added and stirred at 100~300 rpm to volatilize dichloromethane. Once dichloromethane volatilized completely, normal saline for injection was slowly added to a total volume of 200 mL. The solution was mixed well to obtain a curcumin-resveratrol complex solution comprising HS 15. The concentration of solutol HS 15 in the curcumin-resveratrol complex solution comprising HS 15 was approximately 20% (v/v), the weight ratio of resveratrol to curcumin was 1:19, and the concentration of the sum of resveratrol and curcumin in the curcumin-resveratrol complex solution comprising HS 15 was 5 mg/mL.

Preparation of the curcumin-resveratrol complex solution without excipient:
  0.05 g of resveratrol, 0.95 g of curcumin, and 150~200 mL of dichloromethane were mixed together, and stirred at 150~500 rpm at room temperature until curcumin dissolved completely. The mixture was stirred at 100~300 rpm to volatilize dichloromethane. Once dichloromethane volatilized completely, normal saline for injection was slowly added to a total volume of 200 mL. The solution was mixed well to obtain a curcumin-resveratrol complex solution without excipient. The weight ratio of resveratrol to curcumin in the curcumin-resveratrol complex solution without excipient was 1:19, and the concentration of the sum of resveratrol and curcumin was 5 mg/mL.

Six-week-old male Sprague-Dawley rats were used for the experiment. First, 16 rats were fed with high-fat diet (Research Diets, Inc.; Cat #D12492) to induce the accumulation of subcutaneous fat. Feeding was continued until each rat weighed 330±10 g, and the rats were randomly assigned into four groups, which were a HFD group, UL003C-NS group, UL003C-HS group, and UL003C-ELP group, with 4 rats in each group such that there was no statistical difference in the body weight between groups. The body weight of each rat was recorded and defined as the "pre-experimental body weight" of each rat. Then, drugs were administered as follows:

A curcumin-resveratrol complex solution without excipient, a curcumin-resveratrol complex solution comprising HS 15, and a curcumin-resveratrol complex solution comprising ELP were injected to the inguinal subcutaneous fat pads of rats in the UL003C-NS group, UL003C-HS group, and UL003C-ELP group, respectively. Each injection volume was 4 mL per kilogram of body weight (4 mL/kg), such that each injected dosage was 20 mg of curcumin-resveratrol complex per kilogram of body weight (20 mg/kg; 4 mL/kg×5 mg/mL=20 mg/kg). Rats in the HFD group were injected with the same volume of normal saline in the same manner described above.

The injection sites mentioned above were the lower inguinal fat pads of rats. Bilateral injections were administered evenly once a day on day 1, 2, 3, 4, 5, and 6 of the experiment. The rats were fed with high-fat diet for the entire duration of the experiment. Their weight changes were recorded daily, and food and water consumption was recorded weekly. The experiment lasted for 14 days, and the rats were euthanized by $CO_2$ on day 15.

The body weight of each rat was recorded and defined as the "post-experimental body weight" of each rat. The "total body weight gain" of each rat was obtained by subtracting its "pre-experimental body weight" from its "post-experimental body weight". The "relative weight gain" was obtained by dividing the total body weight gain of each group by the total body weight gain of the HFD group.

The bilateral lower inguinal subcutaneous fat pads of rats were dissected and weighed, and the weights of the bilateral lower inguinal subcutaneous fat pads were summed to calculate the amount of lower inguinal subcutaneous fat. The amount of lower inguinal subcutaneous fat of each group was divided by the amount of lower inguinal subcutaneous fat of the control group to obtain the "relative weight of the lower inguinal subcutaneous fat". The data were presented as mean±SD and analyzed by one-way ANOVA. Statistical results were shown as symbols or letters. Different symbols or letters indicates statistically significant difference (p<0.05), and identical symbols or letters indicates no statistically significant difference (p>0.05).

Figure 9A:
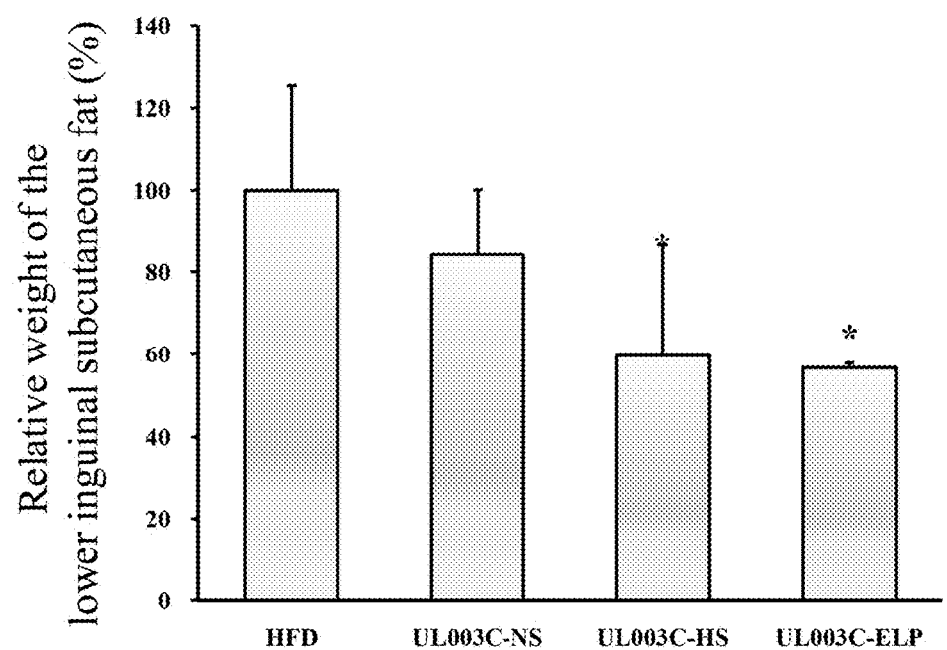
FIG. 9A is the bar chart presenting the relative weight of lower inguinal subcutaneous fat of rats in each group after the rats are fed with a high-fat diet to induce localized fat increasing and locally administered with complex pharmaceutical compositions comprising various excipient via injection.
Figure 9B:
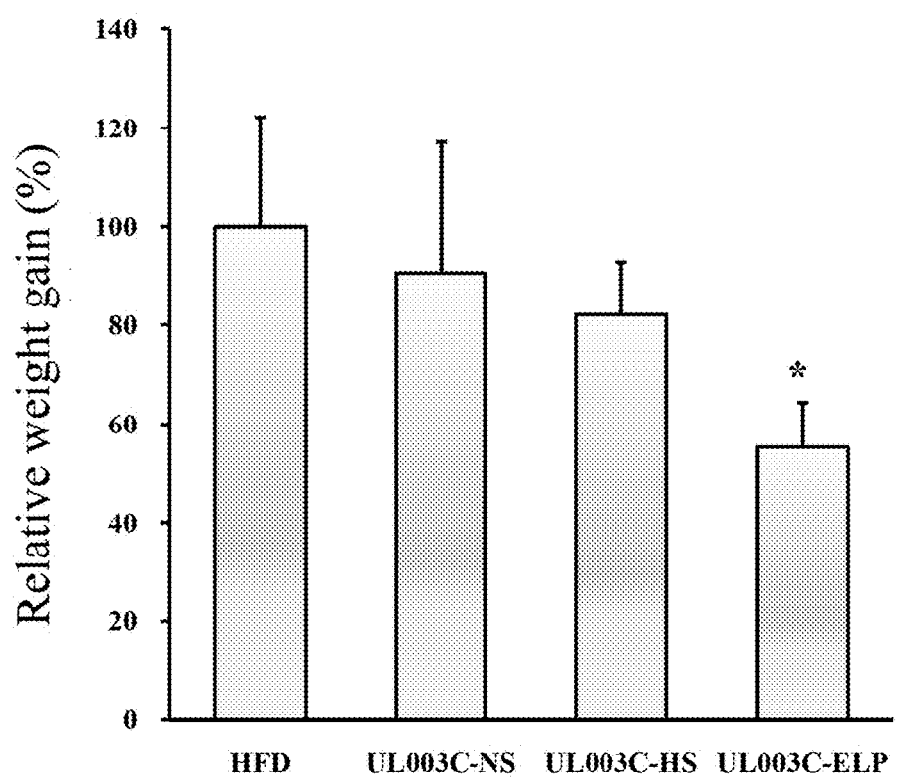
FIG. 9B is the bar chart presenting the body weight gain percentage of rats in each group after the rats are fed with a high-fat diet to induce localized fat increasing and locally administered with complex pharmaceutical compositions comprising various excipient via injection.

Please refer to FIG. 9A and FIG. 9B. FIG. 9A is the bar chart presenting the relative weight of lower inguinal subcutaneous fat of rats in each group after the rats are fed with a high-fat diet to induce localized fat increasing and locally administered with complex pharmaceutical compositions comprising various excipient via injection. FIG. 9B is the bar chart presenting the body weight gain percentage of rats in each group after the rats are fed with a high-fat diet to induce localized fat increasing and locally administered with complex pharmaceutical compositions comprising various excipient via injection.

As shown in FIG. 9A, the relative weight of the lower inguinal subcutaneous fat of rats in the control group was 100±22.3%, the relative weight of the lower inguinal subcutaneous fat of rats in the UL003C-NS group was 84.3±26.6%, the relative weight of the lower inguinal subcutaneous fat of rats in the UL003C-HS group was 59.7±9.1%, and the relative weight of the lower inguinal subcutaneous fat of rats in the UL003C-ELP group was 56.8±12.1%. There was no significant difference in the relative weight of the lower inguinal subcutaneous fat between the UL003C-NS and the control group, suggesting that direct injection of curcumin-resveratrol complex to the subcutaneous fat layer of the administration site cannot reduce the fat at the administration site (localized fat). The relative weight of the lower inguinal subcutaneous fat of the UL003C-HS group was significantly different ($p<0.05$) from that of the HFD group, and the relative weight of the lower inguinal subcutaneous fat of rats in the UL003C-HS group was reduced by 40.3%. The relative weight of the lower inguinal subcutaneous fat of the UL003C-ELP group was significantly different ($p<0.05$) from that of the HFD group, and the relative weight of the lower inguinal subcutaneous fat of rats in the UL003C-ELP group was reduced by 43.2%.

As shown in FIG. 9B, the relative weight gain of rats in the HFD group was 100.0±25.7%, the relative weight gain of rats in the UL003C-NS group was 90.6±15.9%, the relative weight gain of rats in the UL003C-HS group was 82.1±1.1%, and the relative weight gain of rats in the UL003C-ELP group was 55.3±19.1%. Compared to the HFD group, curcumin-resveratrol complex solution without excipient could neither significantly reduce the fat at the administration site (localized fat) ($p>0.05$) nor significantly reduce the body weight ($p>0.05$); curcumin-resveratrol complex solution with HS 15 could significantly reduce the fat at the administration site (localized fat) ($p<0.05$); curcumin-resveratrol complex solution with ELP could significantly reduce the fat at the administration site (localized fat) ($p<0.05$) and significantly reduce the body weight ($p>0.05$).

The experiments above demonstrated that direct injection of curcumin-resveratrol to the subcutaneous fat layer can not reduce the fat at the administration site (localized fat), and can not reduce the body weight. Injection of the curcumin-resveratrol composition comprising the excipient HS to the subcutaneous fat layer can reduce the fat at the administration site (localized fat), but cannot reduce body weight; however, injection of the curcumin-resveratrol composition comprising the non-ionic surfactant ELP to the subcutaneous fat layer can not only reduce the fat at the administration site (localized fat), but can also reduce body weight.

Embodiment 10: The Effect of Different Ratio of Complex Pharmaceutical Composition with Excipient on the Subcutaneous Fat of Rats The preparation of pharmaceutical composition (curcumin solution, resveratrol solution, UL003C solution, UL003R solution, UL005 solution, UL006 solution, UL003C6 solution, or UL003R4 solution) in each group was roughly the same as the experimental procedure in Experiment 9. The only differences were the ratio of resveratrol and curcumin. In this experiment, the guideline of adding all of the ratio of resveratrol and curcumin, the weight of ELP, and the weight of normal saline for injection was shown in Table 1.

In this experiment, the ratios of resveratrol to curcumin in the first group to the eighth group were 0:1, 1:0, 1:19, 9:1, 1:1, 1:30, 1:50, 20:1, respectively, and the final concentrations of resveratrol and curcumin in the pharmaceutical compositions prepared in the first to the eighth group were 5 mg/mL. That is, the preparation method of pharmaceutical composition in the first to the eighth group, the weight ratios of resveratrol to curcumin were 0:1, 1:0, 1:19, 9:1, 1:1, 1:30, 1:50, 20:1, respectively, and the final concentrations of resveratrol and curcumin in the prepared pharmaceutical compositions were 5 mg/mL. Wherein, when the final concentration of drug was presented as mg/mL, it indicated the number of milligrams of resveratrol and curcumin per milliliter of pharmaceutical composition.

TABLE 1

A sample preparation chart for preparing pharmaceutical compositions with ELP

| Group | Ratio of resveratrol to curcumin (weight ratio) | Final concentration of resveratrol and curcumin in the pharmaceutical composition (mg/mL) |
| --- | --- | --- |
| HFD | — | — |
| Curcumin | 0:1 | 5 |
| Resveratrol | 1:0 | 5 |
| UL003C | 1:19 | 5 |
| UL003R | 9:1 | 5 |
| UL005 | 1:1 | 5 |
| UL006 | 1:30 | 5 |
| UL003C6 | 1:50 | 5 |
| UL003R4 | 20:1 | 5 |

There were 9 groups in this experiment, that is, the HFD group, the curcumin group, the resveratrol group, the UL003C group, the UL003R group, the UL005 group, the UL006 group, the UL003C6 group, and the UL003R4 group. The rats were fed and injected in the same manner described in Embodiment 9.

Figure 10A:
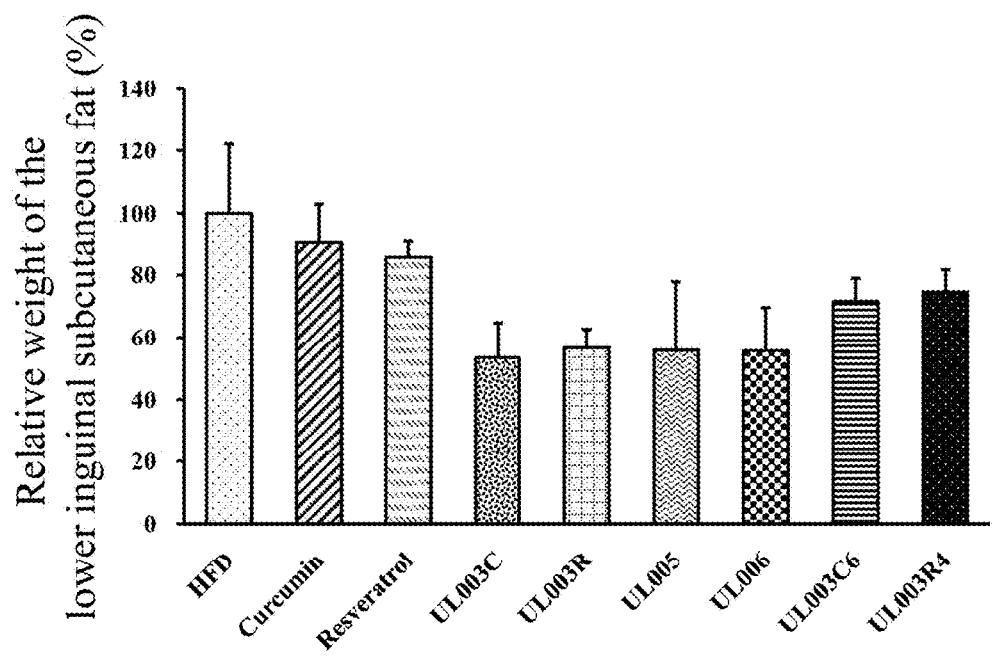
FIG. 10A is the bar chart presenting the relative weight of lower inguinal subcutaneous fat of rats in each group after the rats are fed with a high-fat diet to induce localized fat increasing and locally administered with complex pharmaceutical compositions comprising various weight ratio of medicine via injection.

As shown in FIG. 10A, the relative weight of the lower inguinal subcutaneous fat of rats in the HFD group was 100±22.3%, the relative weight of the lower inguinal subcutaneous fat of rats in the curcumin group was 90.4±12.6%, the relative weight of the lower inguinal subcutaneous fat of rats in the resveratrol group was 85.7±5.1%, the relative weight of the lower inguinal subcutaneous fat of rats in the UL003C group was 53.5±11.2%, the relative weight of the lower inguinal subcutaneous fat of rats in the UL003R group was 56.7±6.0%, the relative weight of the lower inguinal subcutaneous fat of rats in the UL005 group was 55.9±22.0%, the relative weight of the lower inguinal subcutaneous fat of rats in the UL006 group was 55.7±13.9%, the relative weight of the lower inguinal subcutaneous fat of rats in the UL003C6 group was 71.6±7.4%, and the relative weight of the lower inguinal subcutaneous fat of rats in the UL003R4 group was 74.6±7.0%. The relative weight of the lower inguinal subcutaneous fat of the UL003C, UL003R, UL005, UL006, UL003C6, UL003R4 group was significantly different ($p<0.05$) from that of the HFD group. The relative weight of the lower inguinal subcutaneous fat of rats in the UL003C group was reduced by 46.5%. The relative weight of the lower inguinal subcutaneous fat of rats in the UL003R group was reduced by 43.3%. The relative weight of the lower inguinal subcutaneous fat of rats in the UL005 group was reduced by 44.1%. The relative weight of the lower inguinal subcutaneous fat of rats in the UL006 group was reduced by 44.3%. The relative weight of the lower inguinal subcutaneous fat of rats in the UL003C6 group was reduced by 28.4%. The relative weight of the lower inguinal subcutaneous fat of rats in the UL003R4 group was reduced by 25.4%.

Figure 10B:
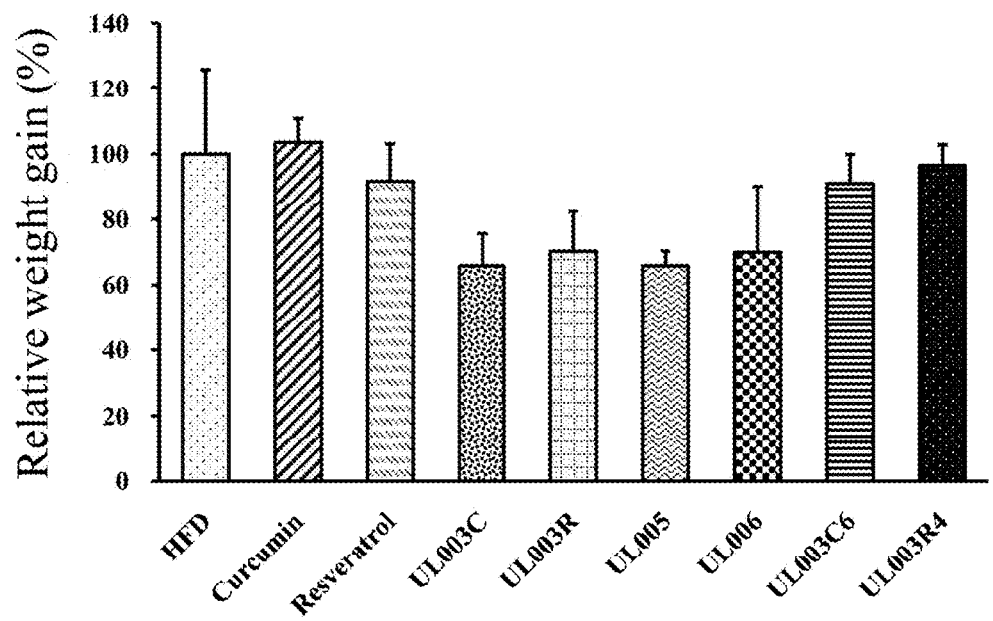
FIG. 10B is the bar chart presenting the body weight gain of rats in each group after the rats are fed with a high-fat diet to induce localized fat increasing and locally administered with complex pharmaceutical compositions comprising various weight ratio of medicine via injection.

As shown in FIG. 10B, the relative weight gain of rats in the HFD group was 100.0±25.7%, the relative weight gain of rats in the curcumin group was 103.6±7.2%, the relative weight gain of rats in the resveratrol group was 91.7±11.4%, the relative weight gain of rats in the UL003C group was 65.9±9.8%, the relative weight gain of rats in the UL003R group was 70.3±12.1%, the relative weight gain of rats in the UL005 group was 65.9±4.5%, the relative weight gain of rats in the UL006 group was 70.0±20.2%, the relative weight gain of rats in the UL003C6 group was 91.1±8.8%, and the relative weight gain of rats in the UL003R4 group was 96.5±6.3%.

Compared to the HFD group, curcumin group, and resveratrol group, the composition UL003C, UL003R, UL005 and UL006 could significantly reduce the fat at the administration site (localized fat) ($p<0.05$) and lead to a trend of body weight loss ($p<0.05$). The experiments above demonstrated that direct injection of the curcumin-resveratrol composition comprising the non-ionic surfactant ELP to the subcutaneous fat layer of the administration site can not only reduce the fat at the administration site (localized fat), but can also lead to a trend of body weight loss.

Please refer to FIG. 11A-F. FIG. 11A-F are the pictures of the subcutaneous fat at the inferior inguinal region of rats of the resveratrol group, UL003R group (R:C=9:1), UL005 group (R:C=1:1), UL003C group (R:C=1:19), UL006 group (R:C=1:30), and curcumin group, respectively from embodiment 10 after they are dissected.

Figure 11A:
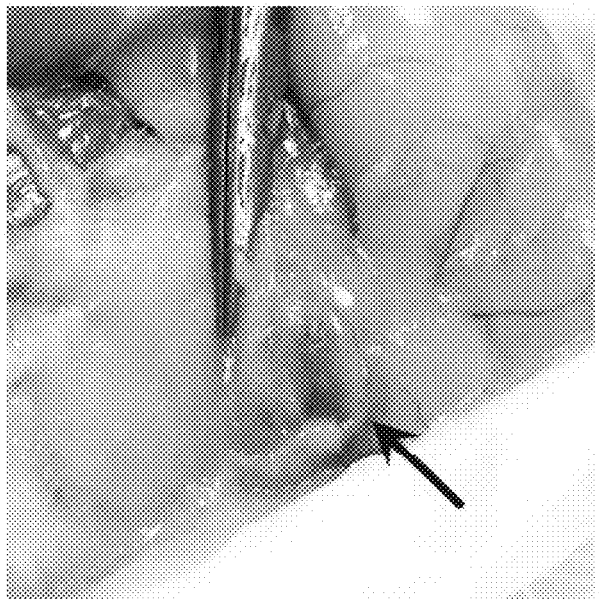
FIG. 11A is a photograph of the adipose tissue in the inferior inguinal region of a rat after the rat was fed with a high-fat diet to induce localized fat increasing and injected with resveratrol at the adipose tissue in the inferior inguinal region.
Figure 11B:
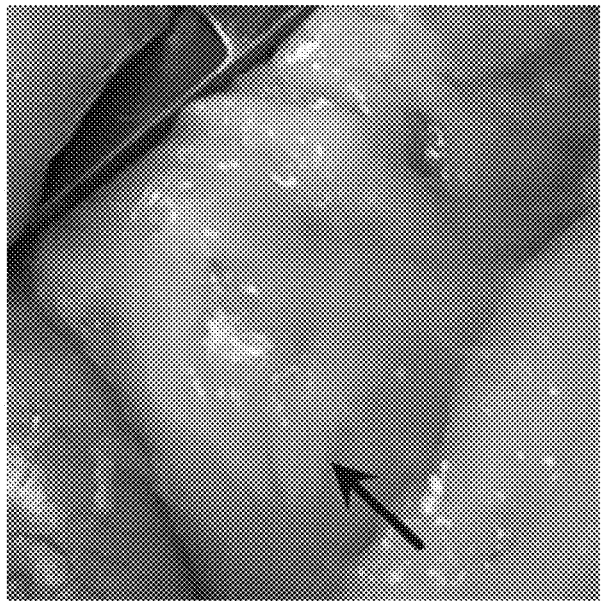
FIG. 11B is a photograph of the adipose tissue in the inferior inguinal region of a rat after the rat was fed with a high-fat diet to induce localized fat increasing and injected with the complex pharmaceutical composition UL003R (resveratrol:curcumin=9:1) at the adipose tissue in the inferior inguinal region.
Figure 11C:
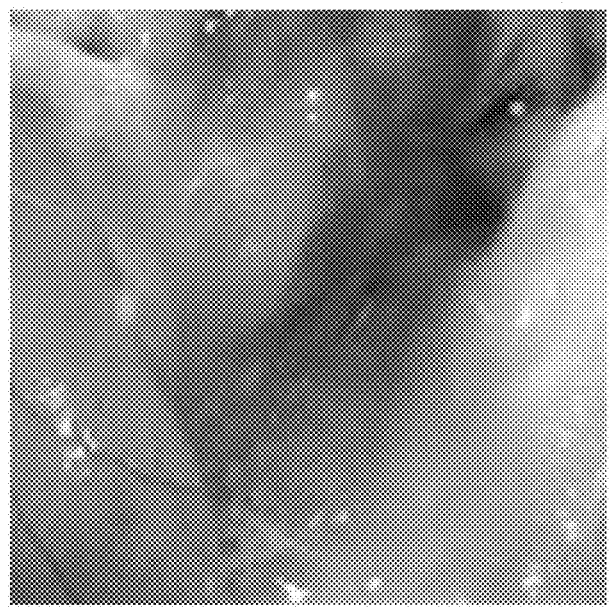
FIG. 11C is a photograph of the adipose tissue in the inferior inguinal region of a rat after the rat was fed with a high-fat diet to induce localized fat increasing and injected with the complex pharmaceutical composition UL005 (resveratrol:curcumin=1:1) at the adipose tissue in the inferior inguinal region.
Figure 11D:
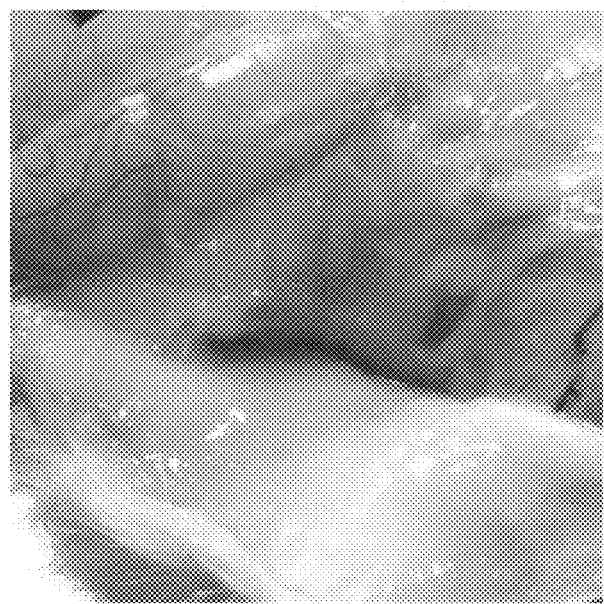
FIG. 11D is a photograph of the adipose tissue in the inferior inguinal region of a rat after the rat was fed with a high-fat diet to induce localized fat increasing and injected with the complex pharmaceutical composition UL003C (resveratrol:curcumin=1:19) at the adipose tissue in the inferior inguinal region.
Figure 11E:
FIG. 11E is a photograph of the adipose tissue in the inferior inguinal region of a rat after the rat was fed with a high-fat diet to induce localized fat increasing and injected with the complex pharmaceutical composition UL006 (resveratrol:curcumin=1:30) at the adipose tissue in the inferior inguinal region.
Figure 11F:
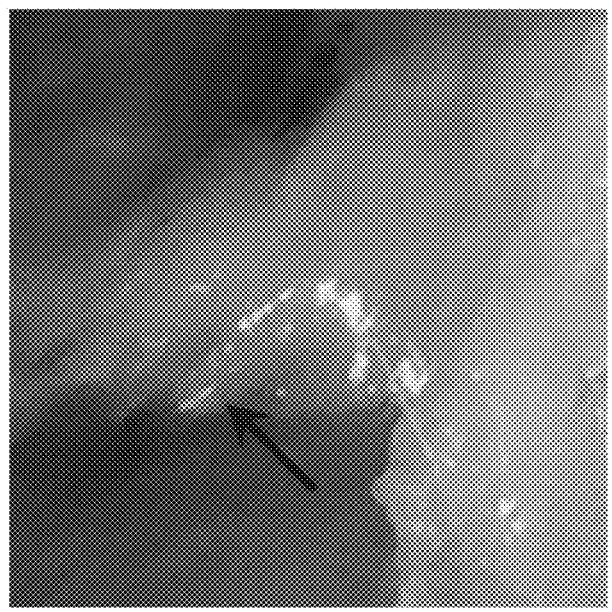
FIG. 11F is a photograph of the adipose tissue in the inferior inguinal region of a rat after the rat was fed with a high-fat diet to induce localized fat increasing and injected with curcumin at the adipose tissue in the inferior inguinal region.

In the resveratrol group, there is ulcer in the rat's inferior inguinal region (please refer to FIG. 11A). In the curcumin group, the curcumin precipitation was observed in the rat's inferior inguinal region (please refer to FIG. 11F). Compared with the resveratrol group and curcumin group, neither ulcer nor curcumin precipitation occurs in the inferior inguinal region of the rats of the UL003R group, UL005 group, UL003C group, or UL006 group. Therefore, as long as the administered drug contains curcumin at the same time, even though only comprises of small amount of curcumin, it could prevent the large area of ulcer caused by resveratrol; as long as the administered drug contains resveratrol at the same time, even though only comprises of small amount of resveratrol, it could prevent curcumin precipitation. In other words, the composition comprising resveratrol and curcumin has an unexpectable effect.

Embodiment 11: Animal Assay by Using Rats (II)

In this experiment, eight-week-old male Sprague-Dawley (SD) rats were used in this experiment. There are three groups, which are control group, UL003C-20 group (20 mg/kg BW, also known as low-dosage group), and UL003C-40 group (40 mg/kg BW, also known as high-dosage group) respectively. Four seven-week-old male rats were used in each group to perform the experiment, the initial weight of the rats were 207 g±6 g. Medication could be administered after the rats of all the groups were fed with high-fat diets consecutively for 2 weeks to make the subcutaneous fat of the rats thicken and make the rats weigh 330 g±10 g. Different dosage of the composition UL003C is subcutaneous injected to subcutaneous fat, the sites to be injected are the bilateral inguinal fat pads, two injection point on each side (5 mg/kg/point), and the total dosages of each rat were 20 mg/kg/time of the subject and 40 mg/kg/time of the subject respectively; the same volume, mL/kg/time, of water for injection was administered to the rats in control group. The injections were performed every other day for three times. Set the day on which the administrations were initiated as the first day, and repeatedly administered the medicine according to above mentioned method on the third day and the fifth day. The change in body weight and the average daily diet intake were recorded every day during the experiment period. After the rat's weight has been weighted for the last time on the twenty-first ($21^{st}$) day, the rats were fasted for 24 hours. Blood was taken to measure the liver and renal function index; the index includes glutamic pyruvic transaminase (GPT), glutamic oxaloacetic transaminase (GOT), creatinine and urea. After rats had been sacrificed, subcutaneous abdominal fat, fat in the superior inguinal region (superior groin), and fat in the inferior inguinal region (inferior groin) were obtained to weight the amount of the subcutaneous fat. Data of all groups are presented in Mean±SD; letters refer to the statistic results, and different letters represent that there are statistical differences among groups ($p<0.05$), same letters represent that there is no statistical difference among groups ($p>0.05$).

Figure 12:
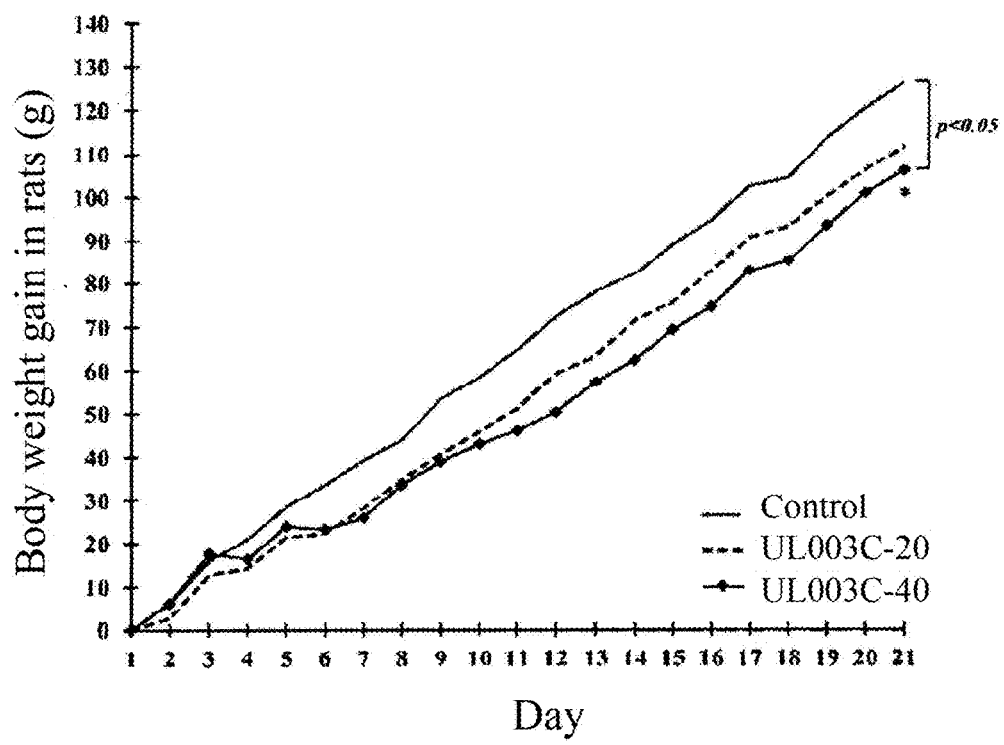
FIG. 12 is the line graph presenting the weight change of rats in each group after the rats are fed with a high-fat diet to induce localized fat increasing and locally administered with medicine via injection in the present invention.

Results are shown as in FIG. 12, the total weight gains of the rats treated with either low-dosage or high-dosage of the composition UL003C of the present invention were lower than the total weight gains of the rats in control group, wherein the amount of weight gain of rats in UL003C-40 group was significantly lower than the weight gain of the rats in control group ($p<0.05$), reduced by 15.8% of weight. Compare with the control group, although the amount of weight gain of rats in UL003C-20 group has a descending trend, decreased by 11.1%, but did not reach significant statistical difference ($p>0.05$). It indicates that the body weight can also be reduced by injecting the composition of the present invention to the subject, and the effect is related to the dosage.

Figure 13:
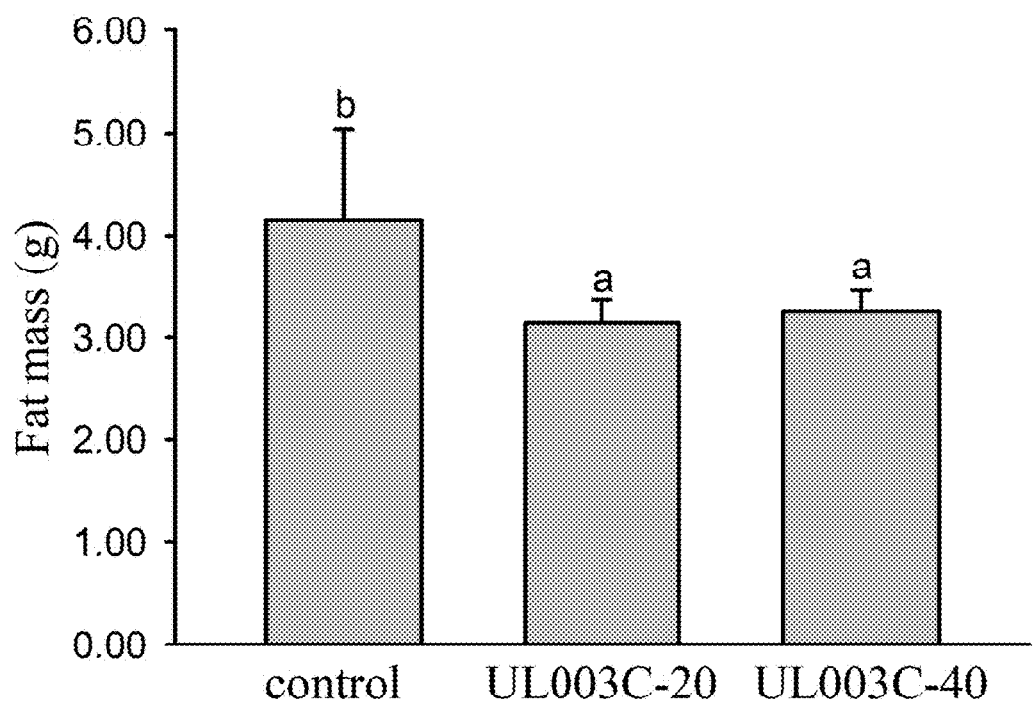
FIG. 13 is the bar chart presenting the subcutaneous fat of rats in each group after the rats are fed with a high-fat diet to induce localized fat increasing and locally administered with medicine via injection in the present invention.

As shown in FIG. 13, it is the result presenting the reduction of subcutaneous fat at the administration site of the rats in each group after sacrifice; compared to control group, the composition UL003C of the present invention could significantly reduce subcutaneous fat around the injection site ($p<0.05$); wherein in the low dosage group, the amount of subcutaneous fat reduction could reach 24.3% at the injection site ($p<0.05$); in the high dosage group, the amount of subcutaneous fat reduction reach 21.6% at the injection site ($p<0.05$).

Figure 14A:
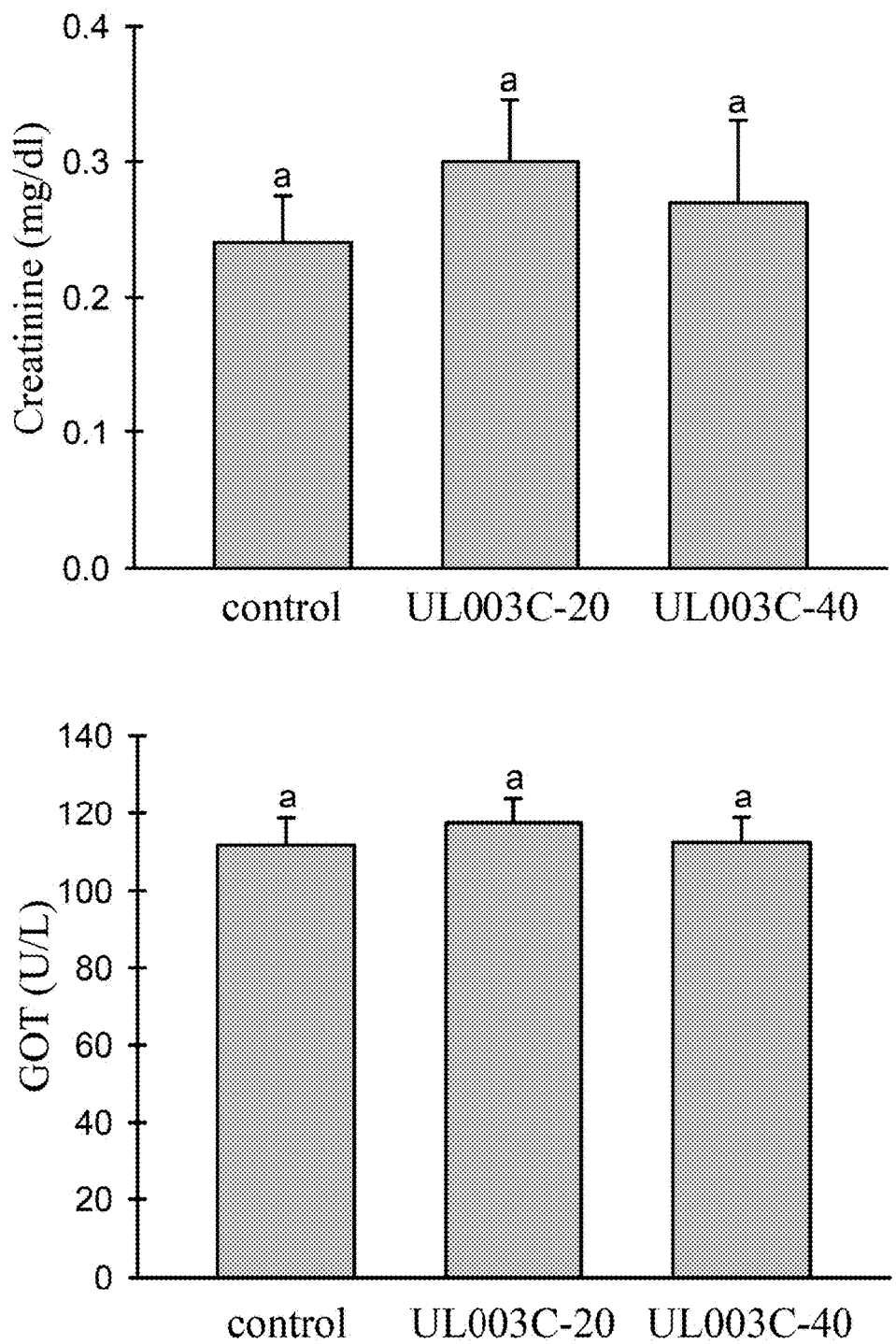
FIG. 14A is the bar chart presenting the serum biochemical values (creatinine and glutamic oxaloacetic transaminase (GOT)) of rats in each group after the rats are fed with a high-fat diet to induce localized fat increasing and locally administered with medicine via injection in the present invention.
Figure 14B:
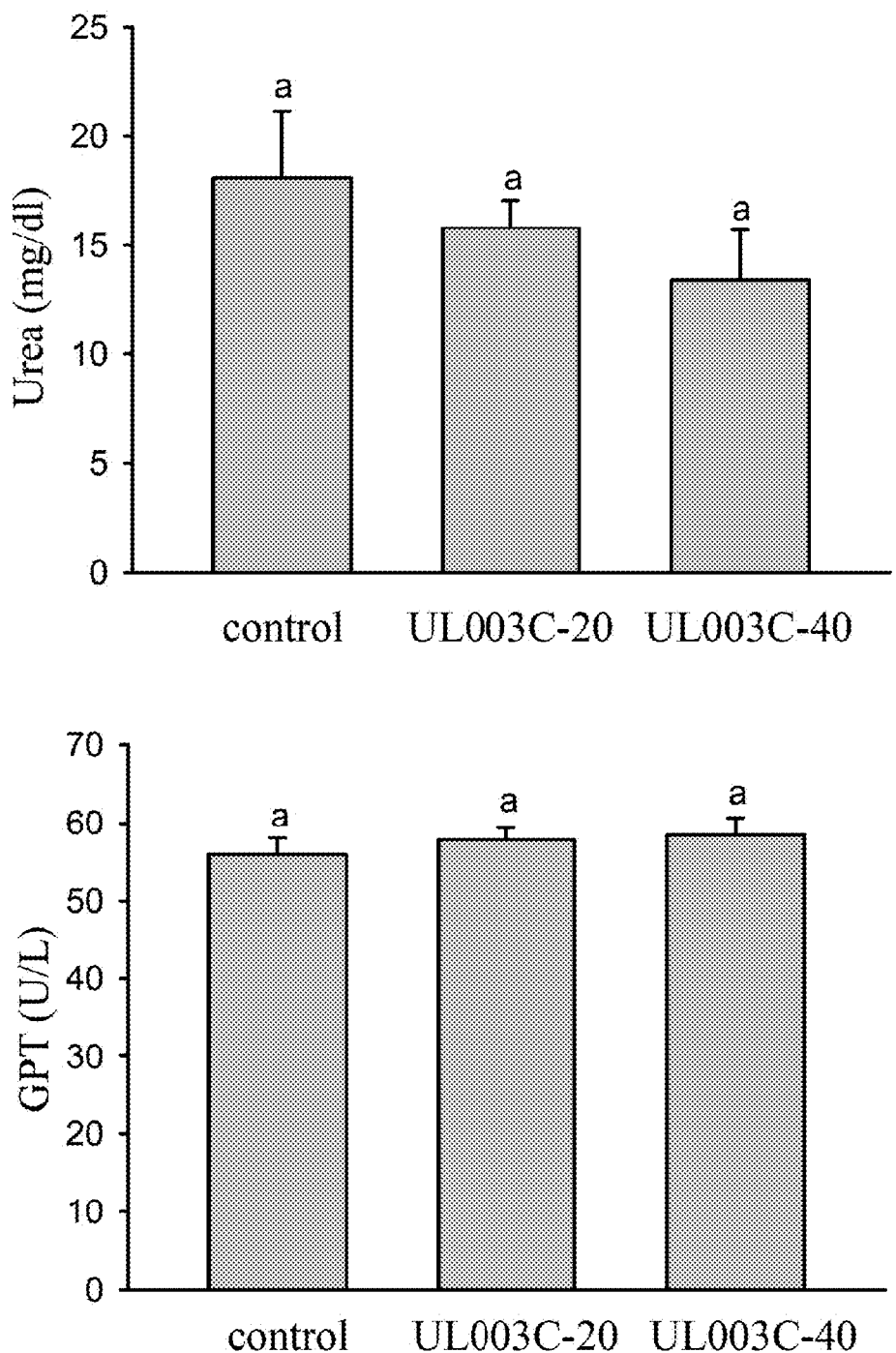
FIG. 14B is the bar chart presenting the serum biochemical values (urea and glutamic pyruvic transaminase (GTP)) of rats in each group after the rats are fed with high-fat diet to induce localized fat increasing and locally administered with medicine via injection in the present invention.

As shown in FIGS. 14A and 14B, the serum biochemical values such as creatinine, urea, GOT, and GPT does not have statistical difference ($p>0.05$). It indicates that the case of injecting either low-dosage or high-dosage of the composition UL003C of the present invention would not affect the safety index; that is, it indicates that the composition of the present invention has good security.

Embodiment 12: Animal Assay by Using Rats (III)

Bcl-2 and Bax are two important regulators in apoptotic pathway, the balance between the two regulators is an important mechanism to regulate apoptosis. Higher Bcl-2 expression suppresses apoptosis while higher Bax expression promotes apoptosis. The high or low ratio between these two proteins could determine that the cells would tend to be survival or initiate apoptosis reaction.

In this experiment, the expression of apoptosis-inhibiting protein Bcl-2 and apoptosis-promoting protein Bax2 in adipose tissue of the subcutaneous injection site of rats in each group was determined by Western blot analysis, and the ratio of Bax and Bcl-2 was used to evaluate the effect of composition UL003C of the present invention on adipocyte apoptosis. In this experiment, the subcutaneous adipose tissues in the inferior inguinal region around the injection sites of the rats sacrificed in example 8 was used to perform protein extract with 450 µl T-PER®, 30 µg of protein of each group was taken to perform polyacrylamide gel electrophoresis (SDS-PAGE) and then transfer the protein to PVDF membrane. The Bcl-2 antibody, model number sc-7382, used in Western blot was purchased from Santa Cruz and, the Bax antibody, model number sc-526, was purchased from Santa Cruz. Data of all groups are presented in Mean±SD; letters refer to the statistic results, and different letters represents that there is statistical difference among groups ($p<0.05$), same letters represents that there is no statistical difference among groups ($p>0.05$).

Figure 15:
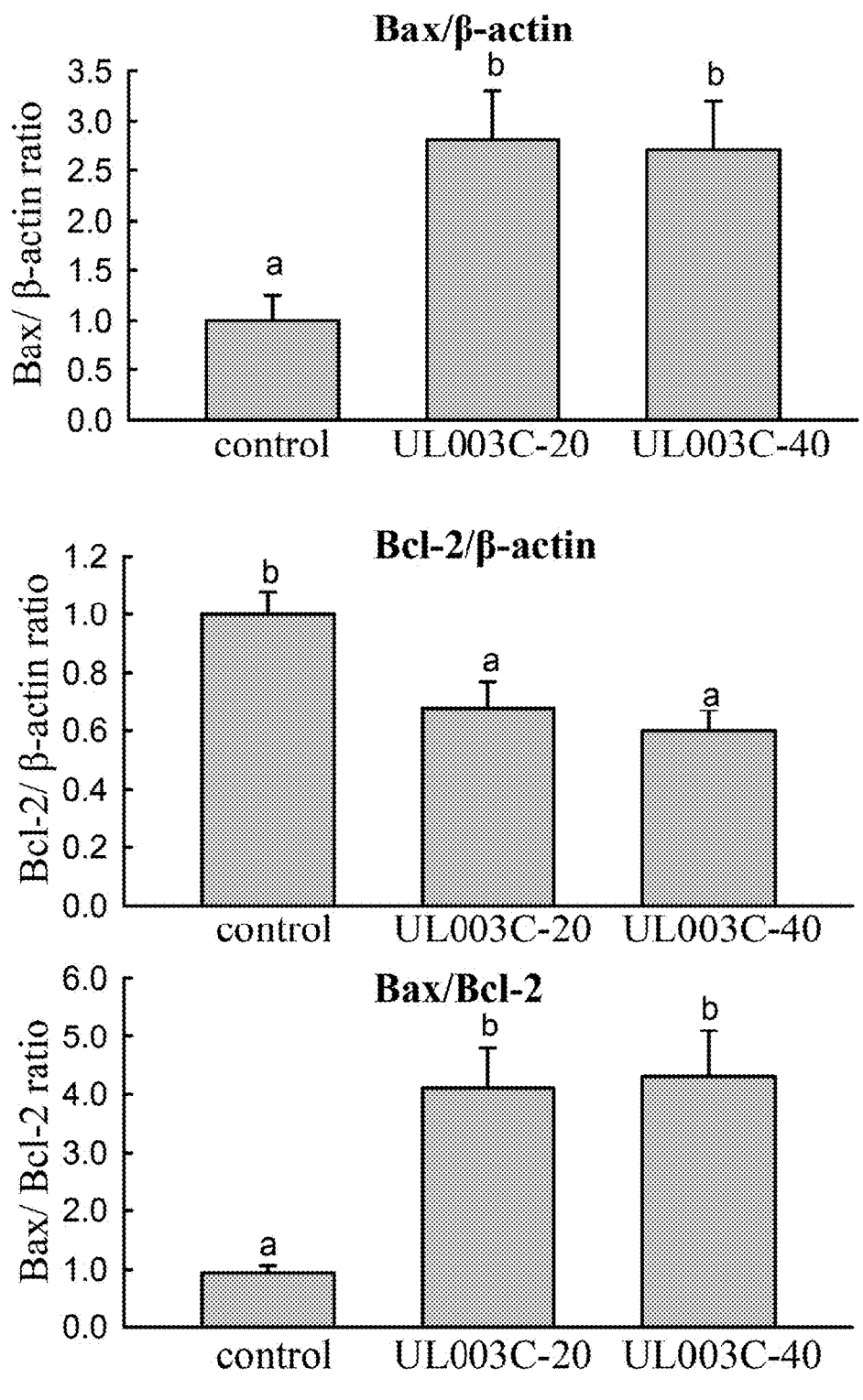
FIG. 15 is the bar chart presenting the expression of apoptosis related protein such as Bax and Bcl-2 and the ratio of Bax/Bcl-2 in each group detected by Western Blotting after the rats are fed with a high-fat diet to induce localized fat increasing and locally administered with medicine via injection in the present invention.

Results are shown as in FIG. 15, compared with control group, either low-dosage or high-dosage of the composition UL003C of the present invention could significantly enhance the Bax expression ($p<0.05$) and significantly inhibit Bcl-2 expression ($p<0.05$), and its Bax/Bcl-2 ratio was significantly higher than that of control group ($p<0.05$). The results indicate that injecting the composition UL003C of the present invention to the rats could effectively induce the adipocytes in the adipose tissue initiating apoptosis. The present invention could indeed and effectively induce adipocyte to initiate apoptosis and reduce its amount of localized fat. The results of animal assays reconfirmed the mechanism that the composition of the present invention could achieve the result of reducing adipocytes and localized fat is via the pathway of promoting adipocyte apoptosis.

The above descriptions are merely the preferred embodiments, and are not limitation to the present invention in any form; even though the preferred embodiments of the present invention are disclosed above, it is not used to limit the present invention by any means. Any technical personnel, as long as it is within the range, without deviation, of the technical skill plan of the present invention, could use the above disclosed technical information to make an embodiment of equal effect with several adjustments or modification, but any information that has not deviated from the technical plans of the present invention, which are any simple modification from the techniques of the present invention made substantially to the above embodiments, still belongs within the range of the technical plan s of the present invention.

What is claimed is:

1. A method for reducing localized fat at a local site of a subject, comprising:
    administering at the local site of the subject a therapeutically effective amount of a pharmaceutical composition comprising resveratrol, and curcumin;
    wherein the weight ratio of resveratrol to curcumin ranges from 1:30 to 9:1.

2. The method as claimed in claim 1, wherein the pharmaceutical composition further comprises a non-ionic surfactant, and the non-ionic surfactant is 2-hydroxyethyl 12-hydroxyoctadecanoate or a polyoxyethylene castor oil derivative.

3. The method as claimed in claim 2, wherein the polyoxyethylene castor oil derivative is PEG-35 castor oil.

4. The method as claimed in claim 1, wherein the subject is an animal or a human.

5. The method as claimed in claim 1, wherein the local site is a localized fat site.

6. The method as claimed in claim 5, wherein the localized fat site is a face, jaw, arm, waist, abdomen, or thighs.

7. The method as claimed in claim 1, wherein the pharmaceutical composition is administered by injection, subcutaneous implantation, implantable infusion, ointment, or patch.

8. The method as claimed in claim 7, wherein the injection is subcutaneous injection.

9. The method as claimed in claim 8, the subcutaneous injection is injected to subcutaneous fat layer.

10. The method as claimed in claim 7, wherein the effective amount of the pharmaceutical composition is from 0.4 mg/kg BW to 100 mg/kg BW.

11. The method as claimed in claim 10, wherein the effective amount of the pharmaceutical composition is from 1 mg/kg BW to 60 mg/kg BW.

12. A method for reducing weight of a subject, comprising:
    administering at a local site of the subject a therapeutically effective amount of a pharmaceutical composition comprising resveratrol, and curcumin;
    wherein the weight ratio of resveratrol to curcumin ranges from 1:30 to 9:1.

13. The method as claimed in claim 12, wherein the pharmaceutical composition further comprises a non-ionic surfactant, and the non-ionic surfactant is a polyoxyethylene castor oil derivative.

14. The method as claimed in claim 12, wherein the local site is a localized fat site.

15. The method as claimed in claim 14, wherein the localized fat site is a face, jaw, arm, waist, abdomen, or thighs.

16. The method as claimed in claim 15, wherein the pharmaceutical composition is administered via subcutaneous injection.

17. The method as claimed in claim 16, the subcutaneous injection is injected to subcutaneous fat layer.

18. The method as claimed in claim 15, wherein the effective amount of the pharmaceutical composition is from 0.4 mg/kg BW to 100 mg/kg BW.

19. The method as claimed in claim 18, wherein the effective amount of the pharmaceutical composition is from 1 mg/kg BW to 60 mg/kg BW.

20. The method as claimed in claim 13, wherein the polyoxyethylene castor oil derivative is PEG-35 castor oil.

* * * * *